US012673102B2

(12) United States Patent
Xie et al.

(10) Patent No.: US 12,673,102 B2
(45) Date of Patent: Jul. 7, 2026

(54) METHOD FOR IMPROVING IMMUNOGENICITY OF PROTEIN/PEPTIDE ANTIGEN

(71) Applicant: SinoCellTech Ltd., Beijing (CN)

(72) Inventors: Liangzhi Xie, Beijing (CN); Yanjing Zhang, Beijing (CN); Jiandong Zhang, Beijing (CN)

(73) Assignee: SinoCellTech Ltd., Beijing (CN)

( * ) Notice: Subject to any disclaimer, the term of this patent is extended or adjusted under 35 U.S.C. 154(b) by 769 days.

(21) Appl. No.: 17/922,335

(22) PCT Filed: Apr. 29, 2021

(86) PCT No.: PCT/CN2021/090809
§ 371 (c)(1),
(2) Date: Oct. 28, 2022

(87) PCT Pub. No.: WO2021/219047
PCT Pub. Date: Nov. 4, 2021

(65) Prior Publication Data
US 2023/0330220 A1 Oct. 19, 2023

(30) Foreign Application Priority Data

May 1, 2020 (CN) .......................... 202010369100.7

(51) Int. Cl.
| | |
|---|---|
| *C07K 16/10* | (2026.01) |
| *A61K 39/00* | (2006.01) |
| *A61K 39/09* | (2006.01) |
| *A61K 39/12* | (2006.01) |
| *A61K 39/145* | (2006.01) |
| *A61K 39/215* | (2006.01) |
| *A61K 39/29* | (2006.01) |
| *A61K 39/385* | (2006.01) |
| *A61P 31/14* | (2006.01) |

(52) U.S. Cl.
CPC .......... *A61K 39/385* (2013.01); *A61K 39/092* (2013.01); *A61K 39/12* (2013.01); *A61K 39/145* (2013.01); *A61K 39/215* (2013.01); *A61K 39/29* (2013.01); *A61K 2039/55505* (2013.01); *A61K 2039/55566* (2013.01); *A61K 2039/55572* (2013.01); *A61K 2039/6037* (2013.01); *A61K 2039/6087* (2013.01); *A61K 2039/70* (2013.01)

(58) Field of Classification Search
CPC ....... A61P 31/14; A61K 39/12; A61K 39/145; A61K 39/215; C07K 16/1002
See application file for complete search history.

(56) References Cited

U.S. PATENT DOCUMENTS

| | | |
|---|---|---|
| 10,159,728 B2 | 12/2018 | Kapre |
| 10,736,952 B2 | 8/2020 | Kapre |

| | | |
|---|---|---|
| 2014/0302084 A1 | 10/2014 | Schneewind et al. |
| 2017/0072043 A1 | 3/2017 | Kapre |
| 2019/0105383 A1 | 4/2019 | Kapre |
| 2021/0008192 A1 | 1/2021 | Malley et al. |
| 2021/0023192 A1 | 1/2021 | Bagnoli et al. |

FOREIGN PATENT DOCUMENTS

| | | |
|---|---|---|
| AR | 114627 A1 | 9/2020 |
| AU | 2018243910 A8 | 11/2019 |
| AU | 2019221496 A1 | 8/2020 |
| BR | 112020016373 A2 | 12/2020 |
| CA | 3061709 A1 | 10/2018 |
| CA | 3090609 A1 | 8/2019 |
| CN | 1355710 A | 6/2002 |
| CN | 103893751 A | 7/2014 |
| CN | 106075428 A | 11/2016 |
| CN | 108289938 A | 7/2018 |
| CN | 108619501 A | 10/2018 |
| CN | 108619502 A | 10/2018 |
| CN | 108619505 A | 10/2018 |
| CN | 108619506 A | 10/2018 |
| CN | 108619507 A | 10/2018 |
| CN | 108619508 A | 10/2018 |
| CN | 110251667 A | 9/2019 |
| CN | 110730670 A | 1/2020 |
| CN | 112153980 A | 12/2020 |
| EA | 202091690 A1 | 11/2020 |

(Continued)

OTHER PUBLICATIONS

Chowdhury et al., "Mucosal vaccination of conserved sM2, HA2 and cholera toxin subunit A1 (CTA1) fusion protein with poly gamma-glutamate/chitosan nanoparticles (PC NPs) induces protection against divergent influenza subtypes", Veterinary Microbiology, 2017, 201:240-251.*

Ji et al., "Design of Fusion Proteins for efficient and soluble production of immunogenic eebola virus glycoprotein in *Escherichia coli* ", Biotechology Journal, 2018, 13:1-9).*

First Office Action, Japanese Patent Application No. 2022-566202, Oct. 24, 2023, Japanese Patent Office, 3 Pages, Japan.

First Office Action, Russian Patent Application No. 2022130021, 6 Pages, Federal Service for Intellectual Property (ROSPATENT), Moscow, Russia.

First Office Action, Russian Patent Application No. 2022130021, 3 Pages, Federal Service for Intellectual Property (ROSPATENT), Moscow, Russia (English Translation).

(Continued)

*Primary Examiner* — Barry A Chestnut

(74) *Attorney, Agent, or Firm* — Smart & Biggar LP

(57) ABSTRACT

Disclosed is a method for improving the immunogenicity of a protein/peptide antigen, the method comprising conjugating a protein/peptide antigen with a sugar to form a sugar-protein/peptide antigen conjugate, which has improved immunogenicity compared to an unconjugated protein/peptide antigen. In particular, the method involves conjugating a pathogen, such as a viral surface protein antigen or a fragment thereof, with a polysaccharide, in particular a capsular polysaccharide of *Streptococcus pneumonia*. The conjugate with improved immunogenicity can be used to prevent or treat diseases caused by pathogens, in particular diseases caused by coronaviruses.

39 Claims, 2 Drawing Sheets

Specification includes a Sequence Listing.

(56) References Cited

FOREIGN PATENT DOCUMENTS

| | | | |
|---|---|---|---|
| EP | 3347042 | A1 | 7/2018 |
| EP | 3600400 | A1 | 2/2020 |
| EP | 3752183 | A1 | 12/2020 |
| GB | 201802339 | | 3/2018 |
| IL | 276661 | | 9/2020 |
| JP | 2002-513028 | | 4/1999 |
| JP | 2002-513028 | A | 5/2002 |
| KR | 20180043352 | A | 4/2018 |
| KR | 20200038339 | A | 4/2020 |
| KR | 20200121825 | A | 10/2020 |
| KR | 20210011083 | A | 1/2021 |
| PH | 12018500305 | A1 | 8/2018 |
| RU | 2420315 | C2 | 6/2011 |
| SG | 11202007676 | R | 9/2020 |
| WO | 9955715 | A2 | 11/1999 |
| WO | 2013022808 | A2 | 2/2013 |
| WO | 2014/060383 | A1 | 4/2014 |
| WO | 2015/110941 | A2 | 7/2015 |
| WO | 2017044932 | A1 | 3/2017 |
| WO | 2018183475 | A1 | 10/2018 |
| WO | 2019158537 | A1 | 8/2019 |
| WO | 2020/058963 | A1 | 3/2020 |
| ZA | 201800928 | B | 6/2019 |

OTHER PUBLICATIONS

Search Report, Russian Patent Application No. 2022130021, 2 Pages, Federal Service for Intellectual Property (ROSPATENT), Moscow, Russia.

Bernhardt, Wiebke, European Search Report, Patent Application No. 21797065.6, 10 pages, European Patent Office, Munich, Germany.

Liu, Cynthia, Research and Development on Therapeutic Agents and Vaccines for COVID-19 and Related Human Coronavirus Diseases, 17 pages, ACS Central Science, 2020, 6, 315-331.

Anonymous, DRAFT landscape of COVID-19 candidate vaccines, 7 pages.

Lang Shuyao et al., Carbohydrate Conjugates in Vaccine Developments, 25 pages, Frontiers in Chemistry, 2020, 8:284, doi:10.3389/fchem.2020.00284.

Vietnamese Office Action, Patent Application No. 1-2022-07360(based on PCT-CN-2021-090809), Apr. 25, 2024, 2 pages, National Office of Intellectual Property of Vietnam (NOIP), Thanh Xuan District, Ha Noi.

Tang, Xiaofan, International Preliminary Report on Patentability, PCT/CN2021/090809, Oct. 27, 2022, 5 pages, The International Bureau of WIPO, Geneva, Switzerland.

Sikora, Dorota, Examiner's Report, Canadian Patent Application No. 3176745, Mar. 14, 2024, 4 pages, Canadian Intellectual Property Office, Gatineau, Quebec.

Tang, Xiaofan, International Preliminary Report on Patentability, PCT/CN2021/090809, Oct. 27, 2022, 5 pages,The International Bureau of WIPO, Geneva, Switzerland. [english translation].

First Office Action issued in corresponding Indonesian Patent Application No. P00202213535 dated May 2, 2025, with English machine translation.

First Office Action issued in corresponding Mexican Patent Application No. MX/a/2022/013456 dated Mar. 18, 2025, with English machine translation.

First Office Action issued in corresponding Chinese Patent Application No. 202180030064.4 with English machine translation.

First Examination Report issued in corresponding Australian Patent Application No. 2021262999 dated Oct. 24, 2024.

Office Action issued in corresponding Brazilian Patent Application No. BR 11 2022 022003 0 dated Sep. 16, 2024 (includes English translation.

First Examination Adverse Report (Sear1) issued in corresponding Malaysian Patent Application No. PI2022006059 dated Dec. 19, 2024.

Notice of Preliminary Rejection issued in corresponding Korean Patent Application No. 10-2022-7041681dated Jul. 31, 2025, with English Translation.

Liu, C. et al.; Research and Development on Therapeutic Agents and Vaccines for COVID-19 and Related Human Coronavirus Diseases, ACS Central Science, 2020, 6, 315-331.

International Search Report dated Aug. 2, 2021, PCT/CN2021/090809.

Frasch, C.E. "Preparation of Bacterial Polysaccharide-protein Conjugates: Analytical and Manufacturing Challenges" Vaccine., vol. 27, Jun. 24, 2009 (Jun. 24, 2009), pp. 6468-6470.

Turner, A.E.B. et al. "Novel Polysaccharide-protein Conjugates an Immunogenic 13-Valent Pneumococcal Conjugate Vaccine for S. Pneumoniae" Synthetic and Systems Biotechnology., vol. 2, Dec. 31, 2017 (Dec. 31, 2017), pp. 49-58.

Amanat, F. et al. "SARS_COV_2RBD_His[Synthetic Construct]" NCBI Genbank QJE37811.1, Apr. 27, 2020 (Apr. 27, 2020), entire document.

* cited by examiner

METHOD FOR IMPROVING IMMUNOGENICITY OF PROTEIN/PEPTIDE ANTIGEN

CROSS REFERENCE TO RELATED APPLICATIONS

This application is a U.S. nationalization under 35 U.S.C. § 371 of International Application No. PCT/CN2021/090809 filed Apr. 29, 2021, which claims the benefit of Chinese patent application 202010369100.7 filed on 1 May 2020. The entire contents of the aforementioned applications are incorporated herein by reference.

FIELD

The present invention relates to the field of immunogenic compositions and, more specifically, to a method for improving the immunogenicity of a protein/peptide antigen by conjugating the protein/peptide antigen with a saccharide, resulting in a glyco-protein/peptide antigen conjugate with increased immunogenicity compared to the unconjugated protein/peptide antigen. More specifically, it involves the conjugation of a pathogen, such as a viral surface protein antigen or fragment thereof, with a polysaccharide, in particular a capsular polysaccharide of *Streptococcus pneumoniae*. The immunogenicity-enhanced conjugate can be used to prevent or treat diseases caused by pathogens, in particular those caused by coronaviruses.

BACKGROUND

When an vertebrate individual is immunized with a vaccine in which an infectious microorganism, toxin, virus or subunits thereof is used as the antigenic components, the aforementioned antigenic component, an exogenous substance for the individual, will elicit or stimulate a memory immune response against the exogenous molecule in the individual, thereby protecting the individual from damage by secondary immune response upon re-exposure to the exogenous molecule.

The term "antigen" is an exogenous substance that is recognized (specifically bound) by an antibody or T-cell receptor, but does not necessarily elicit an immune response. Exogenous substances that can be recognized (specifically bound) by antibodies or T-cell receptors and can elicit specific immunity are called "immunogenic antigens" or "immunogens".

Vaccines that use subunits of infectious microorganisms, toxins, viruses, i.e. cellular structures (bacteria or fungi) or parts of viruses as antigens are non-living vaccines and are widely used for their safety. However, the ability of subunits to elicit a specific immune response is weak, i.e. the antigen is poorly immunogenic.

The traditional means of enhancing immunogenicity is the addition of immune adjuvants. New means of enhancing the immune response are still being explored in ongoing research. One of the important tools is to enhance the immunogenicity of poorly immunogenic antigens by conjugating them with exogenous carrier macromolecules, which has been used successfully for decades, such as commonly seen encephalitis vaccine, *Haemophilus influenzae* b vaccine and pneumonia vaccine, in which the purified capsular polysaccharide (capsularpolymer) were combined with carrier protein in order to produce more effective immunogenic compositions. (Schneerson et al. (1984) *Infect. Immun.* 45:582-591) Commonly used carrier proteins such as tetanus toxoid, tetanus toxoid fragment C, tetanus toxoid non-toxic mutants, diphtheria toxoid, CRM197, other non-toxic mutants of diphtheria toxoid [e.g. CRM176, CRM197, CRM228, CRM45 (Uchida et al. Human *J. Biol. Chem.* 218; 3838 3844, 1973); CRM9, CRM45, CRM02, CRM103 and CRM107, and other mutants. These polysaccharide antigens are non-thymocyte-dependent antigens that do not elicit a cellular immune response thus fails to create an immune memory, they cannot form protective antibodies in children or immune-compromised people. The polysaccharide antigen is conjugated to a T-cell epitope bearing protein carrier, then the conjugate is endocytosed and processed by the antigen-presenting cells or B cells, the peptide fragment of the carrier protein is displayed on the cell surface, activating helper T cells and eliciting a series of immune responses to produce protective antibodies and create immune memory.

However, the effect of bacterial polysaccharides on the immunogenicity of protein/peptide antigens has rarely been reported. U.S. Pat. No. 5,192,540A disclosed vaccines comprising an immunogenic conjugate of a 38,000 dalton or 40,000 dalton outer membrane protein of *Haemophilus influenzae* type B and an oxidized polyribose-ribitol-phosphate polysaccharide fragment of *Haemophilus influenzae* type B, which can be used for immunization against diseases caused by *Haemophilus influenzae* type B. However, "the conjugate vaccines of the present invention are highly immunogenic in animal models. Their antibody responses to PRP were significantly higher than those previously reported. The conjugate vaccines also elicits antibodies to the major protein (38K or 40 k protein) of *Haemophilus influenzae* type B."

U.S. Pat. No. 9,296,795B disclosed the use of an immunogenic polysaccharide-protein conjugate having a polysaccharide antigen (or oligosaccharide fragment thereof, representing one or multiple antigenic epitopes) derived from a hospital pathogen in an immunogenic composition, and the polysaccharide was conjugated to a staphylococcal surface adhesin carrier protein to elicit an antibody response to the polysaccharide antigen and the staphylococcal surface adhesin carrier protein. Although "the conjugate described in the present invention has the unique advantage of inducing the production of antibodies against the polysaccharide antigen and the surface adhesion vector protein, both of which are virulence factors, and conferring immunity to diseases caused by hospital pathogens. In other words, the surface adhesin proteins themselves are capable of conferring immunity to the body, rather than just acting as protein carriers for the polysaccharide antigens. "The titres of surface adhesin protein-specific antibodies elicitd by the stapled surface adhesin protein were similar to those of the non-conjugated surface adhesin protein (FIGS. 17-20). This confirms that the antigenic epitope is not altered by the binding of surface adhesin protein and CP."

In the above two research efforts, they only reported that the protein/peptide antigens conjugated to polysaccharides could cause antibody production, but no enhancement of their immunogenicity was reported.

The inventors' pioneering discovery included the enhancement of the immunogenicity of protein/peptide antigens by conjugating them with saccharides and forming glyco-protein/peptide antigen conjugates.

The inventors speculate that the rationale is that protein aggregates stimulate the body's immune response and produce antibodies more readily than protein monomers. Furthermore, most pattern recognition receptors on the surface of antigen-presenting cells in the animal immune system are associated with saccharides, and saccharides produced by bacteria are an important signal to stimulate the immune system. However, the present invention is not bound by this theory.

SUMMARY

One aspect of the present invention relates to a method for improving the immunogenicity of a protein/peptide antigen, the method comprising forming a glyco-protein/peptide antigen conjugate by conjugating the protein/peptide antigen with a saccharide.

In a specific embodiment of the invention, the saccharide is selected from a polysaccharide, an oligosaccharide or a monosaccharide;

preferably capsular polysaccharide of *Neisseria* encephalitis, capsular polysaccharide of *Haemophilus influenzae* b, capsular polysaccharide of *Streptococcus pneumoniae*, capsular polysaccharide of Group B *Staphylococcus aureus*, dextran, mannan, starch, inulin, pectin, carboxymethyl starch, chitosan and derivatives thereof;

more preferably capsular polysaccharide of *Streptococcus pneumoniae*;

most preferably capsular polysaccharide of *Streptococcus pneumoniae* serotype 14, capsular polysaccharide of *Streptococcus pneumoniae* serotype 6B and capsular polysaccharide of *Streptococcus pneumoniae* serotype 7F, wherein the protein/peptide antigen is selected from a pathogen-associated protein/peptide antigen or a tumor-associated protein/peptide antigen, wherein the pathogen is selected from:

coronavirus, human immunodeficiency virus HIV-1, human herpes simplex virus, cytomegalovirus, rotavirus, EB virus, varicella zoster virus, hepatitis virus, respiratory syncytial virus, parainfluenza virus, measles virus, epidemic mumps virus, human papillomavirus, flavivirus or influenza virus, *Neisseria, Moraxella, Bordetella, Mycobacterium* including *Mycobacterium tuberculosis, Escherichia* including enterotoxigenic *Escherichia coli; Salmonella, Listeria, Helicobacter, Staphylococcus* including *Staphylococcus aureus, Staphylococcus epidermidis; Borrelia, Chlamydia* including *Chlamydia trachomatis, Chlamydia pneumoniae; Plasmodium* including *Plasmodium falciparum; Toxoplasma, Candida;* preferably protein/peptide associated with the pathogen invasion into the host;

more preferably the above pathogens are viruses;

more preferably the above virus is selected from viruses of Coronaviridae, Paramyxoviridae, Orthomyxoviridae, Filoviridae or Flaviviridae, and wherein the tumor is selected from:

diffuse large B-cell lymphoma, follicular lymphoma, other lymphoma, leukaemia, multiple myeloma, mesothelioma, gastric cancer, malignant rhabdomyoma, hepatocellular carcinoma, prostate cancer, breast cancer, bile duct and gallbladder cancer, bladder cancer, brain tumor including neuroblastomas, nerve sheath tumor, glioma, glioblastoma and astrocytoma, cervical cancer, colon cancer, melanoma, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma.

In a specific embodiment of the present invention, the protein/peptide antigen is a protein/peptide comprising viral antigen of Coronaviridae;

preferably coronavirus spike protein;

more preferably coronavirus spike protein S1 subunit;

more preferably the coronavirus spike protein receptor binding region RBD;

or a fragment or variant with immunogenicity of all the above protein/peptide antigen.

In a specific embodiment of the present invention, the coronavirus is SARS-COV-2 or Middle East respiratory syndrome coronavirus.

In a specific embodiment of the present invention, the protein/peptide antigen is a fusion protein of an antigen as defined previously with another protein or peptide.

Preferably, the fusion protein is selected from SARS-COV-2 RBD-mFc; or

SARS-COV-2 RBD-his; or

MERS-COV RBD-his; and

Fc is preferably an IgG Fc fragment, more preferably a human or murine IgG Fc fragment.

In a specific embodiment of the present invention, the protein/peptide antigen comprises the sequence as set forth as any one of SEQ ID NO:1, SEQ ID NO:2, SEQ ID NO:3.

In a specific embodiment of the present invention, the glyco-protein/peptide antigen conjugate has a molecular weight of 400-14000 KDa.

In a specific embodiment of the present invention, the protein/peptide antigen is a protein/peptide comprising viral antigen of Paramyxoviridae;

preferably a paramyxovirus glycoprotein receptor binding region;

preferably paramyxovirus glycoprotein F, glycoprotein G;

or a fragment or variant with immunogenicity of all the above protein/peptide antigen.

In a specific embodiment of the present invention, the Paramyxoviridae virus is a human respiratory syncytial virus.

In a specific embodiment of the present invention, the protein/peptide antigen is a fusion protein of an antigen as previously defined with another protein or peptide; preferably the fusion protein is RSV-gpG-his.

In a specific embodiment of the present invention, wherein the protein/peptide antigen comprises the sequence as set forth as SEQ ID NO:4 and/or SEQ ID NO:12.

In a specific embodiment of the present invention, the protein/peptide antigen is a protein/peptide comprising viral antigen of Orthomyxoviridae;

preferably an orthomyxovirus glycoprotein receptor binding region;

preferably a haemagglutinin (HA) protein and/or a neuraminidase (NA) protein;

or a fragment or variant with immunogenicity of all the above protein/peptide antigen.

In a specific embodiment of the present invention, the orthomyxovirus is an influenza B virus and/or an influenza A H5N1 virus.

In a specific embodiment of the present invention, the protein/peptide antigen is a fusion protein of an antigen as previously defined with another protein or peptide, preferably the fusion protein is Flu-B-HA1-his or H5N1-HA-his.

In a specific embodiment of the present invention, wherein the protein/peptide antigen comprises the sequence as set forth as any one of SEQ ID NO:7 and/or SEQ ID NO:15, SEQ ID NO:8 and/or SEQ ID NO:16.

In a specific embodiment of the present invention, the protein/peptide antigen is a protein/peptide comprising viral antigen of Filovirida;

preferably a filovirus envelope glycoprotein receptor binding region;

preferably the filovirus envelope glycoprotein GP1 and/or GP2;

more preferably the filovirus envelope glycoprotein GP1;

or a fragment or variant with immunogenicity of all the above protein/peptide antigen.

In a specific embodiment of the present invention, the filovirus is Ebola virus.

In a specific embodiment of the present invention, the protein/peptide antigen is a fusion protein of an antigen as defined previously with another protein or peptide, preferably the fusion protein is Ebola-GP-Fc or Ebola-GP1-his;

wherein the Fc is preferably an IgG Fc fragment, more preferably a human or murine IgG Fc fragment.

In a specific embodiment of the present invention, the protein/peptide antigen comprises the sequences as set forth as any one of SEQ ID NO:9 and/or SEQ ID NO:17, SEQ ID NO: 10 and/or SEQ ID NO:18.

In a specific embodiment of the present invention, the protein/antigen is a protein/peptide comprising viral antigen of Flaviviridae;

preferably a viral antigen of Flavivirus or Hepacivirus;

preferably the envelope protein receptor binding region of Flavivirus virus;

preferably at least one of the structural domains EDI, EDII and EDIII of Flavivirus virus envelope protein;

more preferably the structural domain EDIII of Flavivirus virus envelope protein; or preferably the envelope glycoprotein receptor-binding region of Hepacivirus virus;

preferably the Hepacivirus viral envelope glycoprotein E1 and/or E2;

or a fragment or variant with immunogenicity of all the above protein/peptide antigen.

In a specific embodiment of the invention, the Flavivirus virus is preferably a Zika virus; the Hepacivirus virus is preferably a hepatitis C virus.

In a specific embodiment of the present invention, the protein/peptide antigen is a fusion protein of an antigen as previously defined with another protein or peptide, preferably the fusion protein is ZIKV-E-Fc; wherein Fc is preferably an IgG Fc fragment, more preferably a human or murine IgG Fc fragment; or preferably the fusion protein is HCV-E2-his and/or HCV-E1-his.

In a specific embodiment of the present invention, the protein/peptide antigen comprises the sequence as set forth as any one of SEQ ID NO: 11 and/or SEQ ID NO:19, SEQ ID NO:6 and/or SEQ ID NO:14, SEQ ID NO:5 and/or SEQ ID NO:13.

In a specific embodiment of the present invention, the glyco-protein/peptide antigen is further conjugated with a protein carrier.

In a specific embodiment of the invention, the protein carrier is a tetanus toxoid, a tetanus toxoid fragment C, a tetanus toxoid non-toxic mutant, a diphtheria toxoid, CRM197, other non-toxic mutants of diphtheria toxoid, preferably CRM197.

The second aspect of the present invention relates to a glyco-protein/peptide antigen conjugate with increased immunogenicity compared to an unconjugated protein/peptide antigen.

In a specific embodiment of the invention, the saccharide is selected from a polysaccharide, an oligosaccharide or a monosaccharide;

preferably capsular polysaccharide of *Neisseria* encephalitis, capsular polysaccharide of *Haemophilus influenzae* b, capsular polysaccharide of *Streptococcus pneumoniae*, capsular polysaccharide of Group B *Staphylococcus aureus*, dextran, mannan, starch, inulin, pectin, carboxymethyl starch, chitosan and derivatives thereof;

more preferably capsular polysaccharide of *Streptococcus pneumoniae*;

most preferably capsular polysaccharide of *Streptococcus pneumoniae* serotype 14, capsular polysaccharide of *Streptococcus pneumoniae* serotype 6B and capsular polysaccharide of *Streptococcus pneumoniae* serotype 7F;

wherein the protein/peptide antigen is selected from a pathogen-associated protein/peptide antigen or a tumor-associated protein/peptide antigen, wherein the pathogen is selected from:

coronavirus, human immunodeficiency virus HIV-1, human herpes simplex virus, cytomegalovirus, rotavirus, EB virus, varicella zoster virus, hepatitis virus, respiratory syncytial virus, parainfluenza virus, measles virus, epidemic mumps virus, human papillomavirus, flavivirus or influenza virus, *Neisseria, Moraxella, Bordetella, Mycobacterium* including *Mycobacterium tuberculosis, Escherichia* including enterotoxigenic *Escherichia coli; Salmonella, Listeria, Helicobacter, Staphylococcus* including *Staphylococcus aureus, Staphylococcus epidermidis; Borrelia, Chlamydia* including *Chlamydia trachomatis, Chlamydia pneumoniae; Plasmodium* including *Plasmodium falciparum; Toxoplasma, Candida;* preferably protein/peptide associated with the pathogen invasion of the host;

more preferably the above pathogen is virus;

more preferably the above virus is selected from viruses of Coronaviridae, Paramyxoviridae, Orthomyxoviridae, Filoviridae or Flaviviridae, and wherein the tumor is selected from:

diffuse large B-cell lymphoma, follicular lymphoma, other lymphoma, leukaemia, multiple myeloma, mesothelioma, gastric cancer, malignant rhabdomyoma, hepatocellular carcinoma, prostate cancer, breast cancer, bile duct and gallbladder cancer, bladder cancer, brain tumor including neuroblastomas, nerve sheath tumor, glioma, glioblastoma and astrocytoma, cervical cancer, colon cancer, melanoma, endometrial cancer, esophageal cancer, head and neck cancer, lung cancer, nasopharyngeal cancer, ovarian cancer, pancreatic cancer, renal cell cancer, rectal cancer, thyroid cancer, parathyroid tumor, uterine tumor and soft tissue sarcoma.

In a specific embodiment of the present invention, the protein/peptide antigen is a protein/peptide comprising viral antigen of Coronaviridae;

preferably coronavirus spike protein;

more preferably coronavirus spike protein S1 subunit;

more preferably the coronavirus spike protein receptor binding region RBD;

or a fragment or variant with immunogenicity of all the above protein/peptide antigen.

In a specific embodiment of the present invention, the coronavirus is SARS-COV-2 or Middle East respiratory syndrome coronavirus.

In a specific embodiment of the present invention, the protein/peptide antigen is a fusion protein of an antigen as defined previously with another protein or peptide.

Preferably, the fusion protein is selected from SARS-COV-2 RBD-mFc; or

SARS-COV-2 RBD-his; or

MERS-COV RBD-his; and

Fc is preferably an IgG Fc fragment, more preferably a human or murine IgG Fc fragment.

In a specific embodiment of the present invention, the protein/peptide antigen comprises the sequence as set forth as any one of SEQ ID NO:1, SEQ ID NO:2, SEQ ID NO:3.

In a specific embodiment of the present invention, the protein/peptide antigen is a protein/peptide comprising an antigen comprising Paramyxoviridae;

preferably a paramyxovirus glycoprotein receptor binding region;

preferably paramyxovirus glycoprotein F, glycoprotein G;

or a fragment or variant with immunogenicity of all the above protein/peptide antigen.

In a specific embodiment of the present invention, the paramyxovirus is a human respiratory syncytial virus.

In a specific embodiment of the present invention, the protein/peptide antigen is a fusion protein of an antigen as defined previously with another protein or peptide, preferably the fusion protein is RSV-gpG-his.

In a specific embodiment of the present invention, the protein/peptide antigen comprises the sequence as set forth as SEQ ID NO:4 and/or SEQ ID NO:12.

In a specific embodiment of the present invention, the protein/peptide antigen comprises an antigen comprising Orthomyxoviridae;

preferably an orthomyxovirus glycoprotein receptor binding region;

preferably a haemagglutinin (HA) protein and/or a neuraminidase (NA) protein;

or a fragment or variant with immunogenicity of all the above protein/peptide antigen.

In a specific embodiment of the present invention, the orthomyxovirus is an influenza B virus and/or an influenza A H5N1 virus.

In a specific embodiment of the present invention, the protein/peptide antigen is a fusion protein of an antigen as defined previously with another protein or peptide;

preferably the fusion protein is Flu-B-HA1-his or H5N1-HA-his.

In a specific embodiment of the present invention, the protein/peptide antigen comprises the sequences as set forth as any one of SEQ ID NO:7 and/or SEQ ID NO:15, SEQ ID NO:8 and/or SEQ ID NO:16.

In a specific embodiment of the present invention, the protein/peptide antigen comprises an antigen comprising Filoviridae;

preferably a filovirus envelope glycoprotein receptor binding region;

preferably the filovirus envelope glycoprotein GP1 and/or GP2;

more preferably the filovirus envelope glycoprotein GP1;

or a fragment or variant with immunogenicity of all the above protein/peptide antigen.

In a specific embodiment of the present invention, the filovirus is Ebola virus.

In a specific embodiment of the present invention, the protein/peptide antigen is a fusion protein of an antigen as defined previously with another protein or peptide, preferably the fusion protein is Ebola-GP-Fc or Ebola-GP1-his;

wherein the Fc is preferably an IgG Fc fragment, more preferably a human or murine IgG Fc fragment.

In a particular embodiment of the invention, the protein/peptide antigen comprises the sequences as set forth as any one of SEQ ID NO:9 and/or SEQ ID NO:17, SEQ ID NO:10 and/or SEQ ID NO:18.

In a specific embodiment of the present invention, the protein/peptide antigen comprises an antigen comprising Flaviviridae;

preferably a virus antigen of Flavivirus or Hepacivirus;

preferably the envelope protein receptor binding region of Flavivirus virus;

preferably at least one of the structural domains EDI, EDII and EDIII of Flavivirus virus envelope protein;

more preferably the structural domain EDIII of Flavivirus virus envelope protein; or preferably the envelope glycoprotein receptor-binding region of Hepacivirus virus;

preferably the Hepacivirus viral envelope glycoprotein E1 and/or E2;

or a fragment or variant with immunogenicity of all the above protein/peptide antigen.

In a specific embodiment of the invention, the Flavivirus virus is preferably Zika virus; or the Hepacivirus virus is preferably a hepatitis C virus.

In a specific embodiment of the invention, the protein/peptide antigen is a fusion protein of an antigen as previously defined with another protein or peptide;

preferably the fusion protein is ZIKV-E-Fc; wherein

Fc is preferably an IgG Fc fragment, more preferably a human or murine IgG Fc fragment; or preferably the fusion protein is HCV-E2-his and/or HCV-E1-his.

In a specific embodiment of the present invention, the protein/peptide antigen comprises any one of the sequences as set forth as SEQ ID NO:11 and/or SEQ ID NO:19, SEQ ID NO:6 and/or SEQ ID NO:14, SEQ ID NO:5 and/or SEQ ID NO:13.

In a specific embodiment of the present invention, the glyco-protein/peptide antigen conjugate has a molecular weight of 400-14000 KDa.

In a specific embodiment of the present invention, the glyco-protein/peptide antigen is further conjugated with a protein carrier.

In a specific embodiment of the invention, the protein carrier is a tetanus toxoid, a tetanus toxoid fragment C, a tetanus toxoid non-toxic mutant, a diphtheria toxoid, CRM197, other non-toxic mutants of diphtheria toxoid, preferably CRM197.

The third aspect of the present invention relates to an immunogenic composition, comprising the aforementioned glyco-protein/peptide antigen conjugate, immune adjuvants and excipients.

In a specific embodiment of the present invention, the adjuvant is selected from aluminium adjuvant, oil-in-water emulsion adjuvant, MF59, QS-21 and lipid monophosphate A.

The fourth aspect of the invention relates to the use of glyco-protein/peptide antigen conjugate or immunogenic immunogenic compositions for the prevention or treatment of diseases caused by pathogen-associated protein/peptide antigens or tumor-associated protein/peptide as previously defined, preferably the pathogen is a coronavirus, more preferably SARS-COV-2 and/or MERS-COV;

a paramyxovirus, more preferably human respiratory syncytial virus;

an orthomyxovirus, more preferably influenza B virus and/or influenza A H5N1 virus;

a filoviruses, more preferably Ebola virus;

a flaviviruses, preferably Zika virus; or hepatitis C viruses.

The fifth aspect of the invention relates to the use of glyco-protein/peptide antigen conjugate or immunogenic immunogenic compositions in the preparation of vaccines or drugs for the prophylactic treatment of diseases caused by pathogen-associated protein/peptide antigens or tumor-associated protein/peptide as previously defined, preferably the pathogen is a coronavirus, more preferably SARS-COV-2 and/or MERS-COV;

a paramyxovirus, more preferably human respiratory syncytial virus;

an orthomyxovirus, more preferably influenza B virus and/or influenza A H5N1 virus;

a filovirus, more preferably Ebola virus;

a flavivirus, more preferably Zika virus; or hepatitis C virus.

DETAILED DESCRIPTION

Definitions

Figures 1, 2:
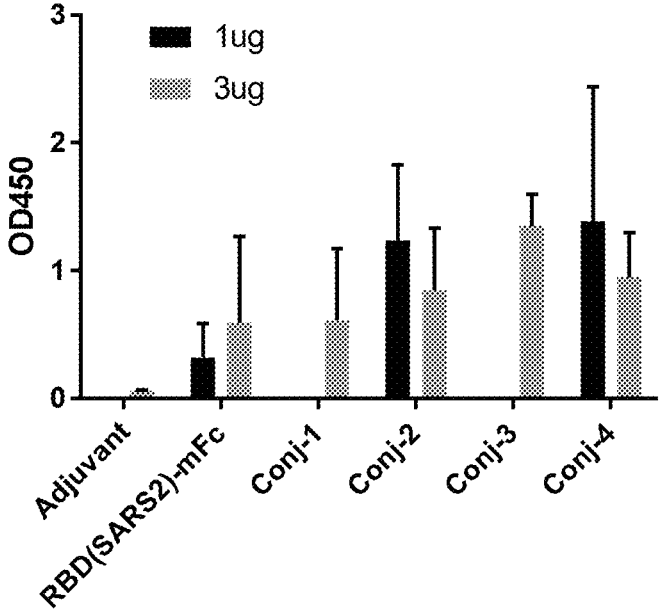
FIG. 1 depicts the anti-SARS-COV-2 RBD antibody titers of mouse sera immunized with an immune combination using SARS-COV-2 RBD-mFc as the antigen. Values are the absorbance detected at 8,000× dilution of the serum.
FIG. 2 depicts a comparison of the different adjuvants with the antigen SARS-COV-2 RBD-his-PS14 conjugate at a serum dilution of 32,000× and an immunisation dose of 3 μg/mouse.

Unless otherwise stated, all technical and scientific terms used herein have the meaning normally understood by a person of ordinary skill in the art to which the present invention belongs. For the purposes of the present invention, the following terms are further defined.

When used herein and in the appended claims, the singular forms "one", "a", "another" and "the" include the plural designation of the object unless the context clearly indicates otherwise.

The terms "include", "comprise" refer to the inclusion of specific components without excluding any other components. Terms such as "consisting essentially of . . . " allow for the inclusion of other components or steps that do not impair the novel or essential character of the invention, i.e. they exclude other unenumerated components or steps that impair the novel or essential character of the invention. The term "consisting of . . . " means including specific components or groups of components and excluding all other components. In this specification and the accompanying claims, "wherein the protein/peptide antigen is a protein/peptide comprising X" means that the amino acid sequence of the protein/peptide antigen comprises the protein/peptide sequence of X.

The term "antigen" is an exogenous substance that is recognized (specifically bound) by an antibody or T-cell receptor, but does not elicit an immune response with certainty. Exogenous substances that elicit specific immunity are called "immunogenic antigens" or "immunogens". A "semi-antigen" is an antigen that cannot elicit an immune response on its own (although a combination of several molecules of semi-antigen, or a combination of semi-antigen and a large molecular carrier, can elicit an immune response).

A "humoral immune response" is an antibody-mediated immune response and involves the introduction and production of antibodies that recognize and bind the antigens in the immunogenic compositions of the invention with a certain affinity, The "cell-mediated immune response" is an immune response mediated by T cells and/or other leukocytes that is elicited by providing antigenic epitopes associated with class I or II molecules of the major histocompatibility complex (MHC), CD1 or other atypical MHC-like molecules.

The term "saccharide" can be used to refer to polysaccharides, oligosaccharides or monosaccharides. The polysaccharide may be isolated from an organism, such as a bacterium, and may be a naturally occurring polysaccharide, optionally sized to a certain degree by microfluidic methods. Resizing the polysaccharide reduces the viscosity of the polysaccharide sample and/or improves the filterability of the conjugated product. Oligosaccharides are hydrolysed polysaccharides with a small number of repeating units (typically, 5 to 30 repeating units). Polysaccharides can also be chemically-synthesised.

The term "conjugate" is used in this specification and the accompanying claims to refer to a protein/peptide covalently conjugated with a saccharide. The glyco-protein/peptide conjugates of the present invention and the immunogenic compositions comprising them may contain a certain amount of free saccharides, protein/peptide.

As used herein, "conjugation" refers to the process whereby a saccharide, such as a bacterial capsular polysaccharide, is covalently linked to a protein/peptide.

The term "immunogenic composition" refers to any pharmaceutical composition containing an antigen, such as a microorganism or component thereof, which can be used to elicit an immune response in an individual.

The term "carrier" may be used to refer to a diluent, adjuvant, excipient or mediator that is administered with the pharmaceutical composition. Water, saline solutions and aqueous solutions of dextrose and glycerol can be used as liquid carriers, particularly for injectable solutions.

As used herein, "immunogenicity" means the ability of an antigen (or epitope of an antigen) such as a coronavirus spike protein receptor binding region or a glycoconjugate thereof or immunogenic composition comprising the same to elicit a humoral or cell-mediated immune response or both in a host (e.g. a mammal).

A "protective" immune response is the ability of an immunogenic composition to elicit a humoral or cell-mediated immune response, or both, to protect an individual from infection. The protection provided need not be absolute, i.e., it need not completely prevent or eradicate infection, as long as there is a statistically significant improvement relative to a control group of individuals (e.g., infected animals not given the vaccine or immunogenic composition). Protection may be limited to moderating the severity of symptoms of infection or the rapidity of attacks.

The terms "immunogenic amount" and "immune effective amount" are used interchangeably herein and mean that the antigen or immunogenic composition is sufficient to trigger an immune response (cellular (T-cell) or humoral (B-cell or antibody) response or both, as measured by standard assays known to those skilled in the art. (as measured by a standard assay known to those skilled in the art).

The effectiveness of an antigen as an immunogen can be measured, for example, by a proliferation assay, by a cytolysis assay, or by measuring the level of B-cell activity.

Method of the Present Invention for Improving the Immunogenicity of Protein/Peptide Antigens The present invention is a pioneering invention in which the inventors find that the immunogenicity of a protein/peptide antigen is improved including by conjugating the protein/peptide antigen with a saccharide to form a glyco-protein/peptide antigen conjugate.

Prior to this invention, no studies had reported increase of the immunogenicity of protein/peptide antigens in glyco-protein/peptide antigen conjugate. In contrast, as mentioned in the background art, previous studies described immuno-genicity of protein/peptide antigens in the conjugates as preserved immunogenicity (U.S. Pat. No. 5,192,540A/U.S. Pat. No. 9,296,795B) or that the protein/peptide antigen epitopes were not altered by conjugation (U.S. Pat. No. 9,296,795B). These teachings are contrary to the purpose of the present invention.

The Glyco-Conjugated Protein/Peptide Antigens of the Invention

1. Coronaviridae Viruses as Antigens

The Coronaviridae family includes the Orthocoronavirinae and Letovirinae subfamilies.

The betacoronaviru genus of Orthocoronaviridae subfamily contains the well-known Severe Acute Respiratory Syndrome coronavirus (SARS-COV), Middle East respiratory syndrome-related coronavirus (MERS-COV), and the Severe Acute Respiratory Syndrome Coronavirus 2 (SARS-COV-2). These three viruses mediate viral invasion primarily through the binding of spike protein (S protein) to host cell receptors and determine viral tissues or host tropism. The host cell receptor protein for SARS-COV-2 is angiotensin-converting enzyme 2 (ACE2). The spike protein (S protein) binds to the ACE2 receptor and is cleaved by the host protease into the S1 polypeptide containing the Receptor binding domain (SARS-COV-2 RBD) and the S2 polypeptide responsible for mediating the fusion of the virus with the cell membrane and thus invading the host.

In one embodiment of the invention, the coronavirus SARS-COV-2 spike protein (SARS-COV-2 S protein), its extracellular region, the S1 subunit or the receptor binding region are used as antigens.

In one embodiment of the invention, Middle East Respiratory Syndrome coronavirus is selected as an antigen. e.g. its extracellular region, S1 subunit or receptor-binding region is used as antigen.

2. Paramyxoviridae Viruses as Antigens

The Paramyxoviridae family comprises two subfamilies, Paramyxivirinae and Pneumovirinae. Human respiratory syncytial virus (RSV) is one of the respiratory viruses of the genus Respirovirus in the subfamily Paramyxivirinae. RSV encodes two major transmembrane surface glycoproteins, glycoprotein G (adsorption protein) and glycoprotein F (fusion protein). Glycoprotein G mediates viral binding to cellular receptors, while glycoprotein F facilitates viral fusion to the cell membrane, allowing viral ribonucleoproteins to invade the cytoplasm (Lopez et al. (1998) *J. Virology* 72:6922-6928).

In one embodiment of the invention, RSV envelope glycoproteins are selected as antigens. Human RSV envelope glycoprotein, such as RSV glycoprotein F or glycoprotein G, can be used.

3. Orthomyxoviridae Viruses as Antigens

The Orthomyxoviridae family includes Influenzavirus A, Influenzavirus B, Influenzavirus C and other genera. Influenza virus A, B and C infections rely primarily on two envelope proteoglycans: haemagglutinin (HA) and neuraminidase (NA), which are responsible for viral attachment and cellular invasion into viral particles. Influenza virus infection is triggered by attachment of the haemag-glutinin (HA) protein to sialic acid-containing cell receptors (glycoproteins and glycolipids) on the surface of the virion. The neuraminidase (NA) protein mediates the processing of the sialic acid receptor and viral invasion of cells is dependent on HA-dependent receptor-mediated cytokinesis (CN103865892B).

In one embodiment of the invention, the influenza A H5N1 haemagglutinin (HA) protein is used as an antigen, and the influenza B haemagglutinin protein (HA1 subunit) could also used as an antigen.

4. Filoviridae Viruses as Antigens

The Filoviridae are represented by the ebolaviruses of the genus Ebolavirus and the marburgviruses of the genus Marburgvirus.

The only protein present on the surface of Ebola viruses is the glycoprotein (GP). The trimer of GP1,2 which forms the surface spike of the virus and is composed of two subunits, GP1 and GP2, linked by disulfide bonds (Volchkova, VA ef a/., (1998), *Virology* 250:408-414; Falzarano, D. et al. (2006) Chembiochem 7:1605-1611). GP1 is known to mediate viral attachment to host cells and GP2 is involved in membrane fusion (Sanchez, A. et al., (1996), *Proc Natl Acad Sci USA* 93:3602-3607; Alazard-Dany, N. et al., (2006), *J. Gen. Virol.* 87:1247-1257).

In one embodiment of the invention, the Ebola virus glycoprotein (GP) is selected as an antigen. Such as the GP extracellular structural domain, subunit GP proteins (GP1 and/or GP2).

5. Flaviviridae Viruses as Antigens

The Flaviviridae family of viruses mainly includes the genera Flavivirus, Pestivirus, Pegivirus and Hepacivirus, wherein the Flaviviridae include Zika virus (ZIKV), Dengue fever (DV), West Nile virus, Japanese encephalitis virus and yellow fever virus. The Hepacivirus includes hepatitis C virus (HCV).

The flavivirus envelope protein plays an important role in host cell virus infection, mediating the entry of the virus into the host cell. It consists of three separate structural envelope domains I, II and III (EDI, EDII and EDIII). EDI is a structural central domain of the envelope protein that stabilises the overall orientation of the protein, and glycosylation sites in EDI are associated with viral production, pH sensitivity and neuroinvasiveness. EDII plays an important role in membrane fusion due to the immunological advantages of fusion loop epitopes and envelope dimeric epitopes. In addition, EDIII is a major target for neutralizing antibodies (Xingcui Zhang. et al., (2017) *Viruses.* 2017 November; 9 (11): 338. Structures and Functions of the Envelope Glyco-protein in Flavivirus Infections).

The Zika virus envelope protein ("E" or "EP") consists of three distinct structural domains. E structural domain I (E-DI) is the central structural domain that organizes the entire E protein structure. E structural domain II (E-DII) is formed by two extended loops that protrude from E-DI and are located in pockets at E-DI and E structural domain III (E-DIII). E-DIII is an immunoglobulin-like structural domain, which forms small protrusions on the surface of otherwise smooth, spherical, mature viral particles and is thought to interact with cellular receptors on target cells (CN109996560A).

The HCV RNA genome encodes a single multimeric protein that cleaves into three structural proteins (core, glycoproteins E1 and E2) and seven non-structural proteins (p7, NS2, NS3, NS4A, NS4B, NS5A and NS5B) upon translation or post-translation. The envelope proteins, glycoproteins E1 and E2, form heterodimers and constitute the viral envelope proteins, which play an important role in mediating viral entry and morphogenesis when the virus enters the host cell. The hepatitis C virus envelope proteoglycans bind to specific proteins on the surface of the host hepatocyte to initiate the entry process. This process involves a large number of host receptors/co-receptors. Wherein, E2 is the major HCV envelope proteoglycan and interacts directly with the receptor/co-receptor. It has long been thought that E1 does not interact directly with the host receptor during this process, but rather that it elicits membrane fusion in conjunction with E2 by maintaining a functional E2 conformation required for receptor binding (Yimin, Tong. Et al., (2018) *Front Immunol.* 2018; 9:1411. Role of Hepatitis C Virus Envelope Glycoprotein E1 in Virus Entry and Assembly).

In one embodiment of the present invention, Zika virus envelope protein E-DIII is selected as the antigen.

In one embodiment of the present invention, the hepatitis C virus envelope glycoprotein E1 and/or E2 is selected as antigens.

The viral antigens described above in this chapter can be obtained by extraction of natural pathogens or by genetic recombination. The modified version thereof, e.g. the immunogenic fragments or variants thereof as well as e.g. fusion proteins thereof with purified tags or with antibody Fc fragments, can be used in the present invention. The polysaccharides can be bacterial polysaccharides such as the common capsular polysaccharide of *Neisseria* encephalitis, capsular polysaccharide of *Haemophilus influenzae* b, capsular polysaccharide of *Streptococcus pneumoniae*, capsular polysaccharide of group B *Staphylococcus aureus*, as well as dextran and mannan and so on. The polysaccharides may also be plant-derived polysaccharides such as starch, inulin, pectin, etc., or derivatives of chemically modified polysaccharides, such as carboxymethyl starch. The polysaccharides may also be polysaccharides of animal origin, such as chitosan and its derivatives.

The process of polysaccharide protein conjugation is as follows: the polysaccharide is made to carry a reaction active group by a chemical reaction. The active groups then react with chemically reactive groups on the protein molecule such as the amino, carboxyl, sulfhydryl groups, the imidazole ring on histidine, the indole ring on tryptophan, the phenyl ring on tyrosine, the phenyl ring on phenylalanine, the hydroxyl group on serine and glutamine and asparagine to form the covalent bonds One method of conjugating polysaccharides to protein molecules is to oxidise the polysaccharide with sodium periodate to produce an aldehyde group on the polysaccharide, which reacts with the amino group on the protein molecule to form a Schiff base, which is reduced to a stable single bond in the presence of reducing agents. Thereby the polysaccharide forms a covalent linkage with the protein molecule. A reducing agent such as sodium cyanoborohydride can be added to the reaction system.

Another method of conjugating polysaccharides to protein molecules is the reaction of the polysaccharide with cyanogen bromide or 1-cyano-4-dimethylaminopyridine tetrafluoroborate to produce a reactive cyanate ester. The cyanate group reacts with the amino group on the surface of the protein to form a covalent. The activated polysaccharide can also be reacted first with a linker arm such as hexanediamine, hexanedihydrazide, etc. The product is then reacted with the protein in the presence of a condensinging agent to form a covalent linker.

Polysaccharides can also be activated with other chemical reagents and then reacted with proteins to form a conjugate. Such as epichlorohydrin, triazine, diazine, divinyl sulfone and other reagents that are well known in the art.

To improve the immunogenicity of the glyco-protein/peptide antigen conjugate of the present invention, a protein carrier can be further added to the reaction of the saccharide with the protein/peptide antigen conjugate to form a glyco-protein/peptide antigen-protein carrier conjugate. The protein carrier may be tetanus toxoid, tetanus toxoid fragment C, tetanus toxoid non-toxic mutant, diphtheria toxoid, CRM197, other non-toxic mutants of diphtheria toxoid, preferably CRM197, which are commonly used in the vaccine industry.

Immunogenic Compositions of the Present Invention

In one embodiment, the immunogenic composition of the present invention further comprises at least one of an adjuvant, buffer, cryoprotectant, salt, divalent cation, non-ionic detergent, free radical oxidation inhibitor, diluent or carrier. In one embodiment, the adjuvant in the immunogenic composition of the present invention is an aluminium-based adjuvant. In one embodiment, the adjuvant is an aluminium-based adjuvant selected from aluminium phosphate, aluminium sulphate and aluminium hydroxide. In one embodiment, the adjuvant is aluminium phosphate. An adjuvant is a substance that enhances the immune response when administered together with an immunogen or antigen. The compositions used in the present invention may or may not contain a vaccine adjuvant. Adjuvants that may be used in the compositions of the present invention include, but are not limited to:

Oil emulsion compositions including squalene-water emulsions, e.g. MF59; Complete Freund Adjuvant (CFA) and Incomplete Freund Adjuvant (IFA); Saponin formulations; Combination of saponin and cholesterol to form unique particles called Immunostimulatory Complexes (ISCOM); Virosomes and virus-like particles; The adjuvant used will depend on the individual being administered the immunogenic composition, the prescribed route and frequency of administration.

The immunogenic composition may optionally comprise a pharmaceutically acceptable carrier. The pharmaceutically acceptable carriers include carriers of animals (including human as well as non-human mammals) as documented or to be documented in national pharmacopoeias. The term "carrier" may be used to refer to a diluent, adjuvant, excipient or medium that is administered with the pharmaceutical composition. Water, saline solutions as well as aqueous dextrose and glycerol solutions may be used as liquid carriers, particularly for injectable solutions. The immunogenic compositions of the invention may also comprise one or more additional immunomodulators, which are substances that perturb or alter the immune system so that an up- or down-regulation of humoral and/or cell-mediated immunity is observed. In one embodiment, an up-regulation of the humoral and/or cell-mediated capacity (arms) of the immune system is provided. This includes, for example, adjuvants or cytokines.

Routes of Administration of the Immunogenic Compositions of the Present Invention Immunogenic compositions of the invention for therapeutic or prophylactic treatment can be administered intramuscularly, intraperitoneally, intradermally or subcutaneously; or via mucous membranes to the oral/esophageal, respiratory, genitourinary tract. Intranasal administration of the vaccine is preferred for the treatment of certain diseases, such as preferably pneumonia or otitis media. Although the vaccine of the invention can be given in a single dose, its components can also be co-administered simultaneously or at different time. In addition to a single route of administration, two different routes of administration can be used.

The optimal amount of a component for a particular immunogenic composition can be determined by standard studies involving the observation of an appropriate immune response in individuals. Following the initial vaccination, individuals may receive one or several adequately time-intervaled booster immunizations.

Uses of the Immunogenic Compositions of the Present Invention

The protein/peptide antigen conjugates and immunogenic compositions of the present invention can prevent or treat diseases caused by pathogens such as coronaviruses, paramyxoviruses, orthomyxoviruses, filoviruses and flaviviruses, and more particularly SARS-COV-2 and/or MERS-COV viruses, human respiratory syncytial virus, influenza B virus, influenza A H5N1 virus, Ebola virus, Zika virus and/or hepatitis C virus.

Abbreviations of the Invention

SARS-COV-2 RBD-mFc: SARS-COV-2 coronavirus spike protein receptor-binding region-mouse Fc fusion protein;

SARS-COV-2 RBD-his: SARS-COV-2 coronavirus spike protein receptor binding region with a 6-histidine tag;

MERS-COV RBD-his: Middle East respiratory syndrome coronavirus spike protein receptor binding region with a 6-histidine tag;

RSV-gpG: Human respiratory syncytial virus glycoprotein G;

HCV-E1: Hepatitis C virus Envelope Glycoprotein E1;

HCV-E2: Hepatitis C virus Envelope E2 Protein;

flu-B-HA1: Influenza B Hemagglutinin Protein (HA1 Subunit);

H5N1-HA: Influenza A H5N1 Hemagglutinin;

Ebola-GP: Ebola virus Glycoprotein (Receptor Binding Domain);

Ebola-GP1: Ebola virus Glycoprotein GP1;

ZIKV-E: Zika virus Envelope protein (Domain III);

PS14: capsular polysaccharide of *Streptococcus pneumoniae* serotype 14

PS7F: capsular polysaccharide of *Streptococcus pneumoniae* serotype 7F

Alum: aluminium adjuvant, in this case is aluminium phosphate adjuvant

Example 1: Preparation of Capsular Polysaccharide of *Streptococcus pneumoniae* Serotype 14 (PS14) and 7F (PS7F)

Serotype 14 *Streptococcus pneumoniae* seeds were ATCC 6314 and serotype 7F *Streptococcus pneumoniae* seeds were ATCC 10351.

0.5 mL of glycerol-preserved *Streptococcus pneumoniae* seeds were added to 500 ml of Hoeprich's medium (V. M.

Goncalves, Optimization of medium and cultivation conditions for capsular polysaccharide production by *Streptococcus pneumoniae* serotype 23F, *AllpMicrobiolBiotechnol* (2002) 59:713-717) at 37° C. in a shaker at 150 rpm for 10-16 hours and the culture was stopped when OD600 was above 1.0. Add 0.6 g of sodium deoxycholate, mixed well and left to stand for 2 hours or more to allow complete lysis of the bacteria. Centrifuged at 14000 g for 30 minutes, the removed the supernatant and concentrate by ultrafiltration with 100 kDa to one tenth of the original volume, approximately 400 ml. Gradually added 36% acetic acid into the concentrate and adjusted to pH 3.5. Leave for 2 hours, centrifuged at 14000 g for 30 minutes, removed 390 ml of supernatant and mixed with 130 ml of anhydrous ethanol and left overnight. The next day the supernatant was centrifuged at 14000 g for 30 minutes, add 780 ml of anhydrous ethanol into the supernatant and leave to stand overnight. The next day the supernatant was discarded after 30 minutes of centrifugation at 14000 g. 300 ml of 75% ethanol was added to the precipitate and the precipitate was suspended and then centrifuged again at 14000 g for 30 minutes. The supernatant was discarded and the precipitate was dissolved in 10 ml of water to manage the concentration of polysaccharide in the solution to be greater than 10 mg/ml. The resulting solution is the *Streptococcus pneumoniae* capsular polysaccharide solution.

Example 2: Hydrolysis, High and Low Activation Degree Activation of Polysaccharides The polysaccharide was a *Streptococcus pneumoniae* serotype 14 (PS14) and 7F (PS7F) capsular polysaccharide prepared in Example 1 or dextran (dextran, Sigma, 00894, same below).

2.1 Polysaccharide Hydrolysis.

10 mL of 10 mg/ml purified capsular polysaccharide was added to 0.86 ml of 36% acetic acid, the final concentration of acetic acid in the solution was 500 mM. After a water bath at 90° C. for 2 h, 1 M NaOH was added to neutralize to pH 6-7 to obtain a hydrolysed polysaccharide sample.

The molecular weight of PS14 polysaccharide was determined by HPLC-MALS to be about 500 KDa and about 300 KDa after hydrolysis.

The molecular weight of PS7F capsular polysaccharide was approximately 700 KDa and was not hydrolysed. Dextran was not hydrolysed.

2.2 High Activation Degree Activation of Polysaccharides.

100 mg of sodium periodate was added to 10 mL of 10 mg/ml polysaccharide solution, mixed well and left to react for 1 h in dark. A centrifugal chromatography column containing 5 ml of Sephadex G 25 packing was taken and 10 ml of 50 mM, pH=7.0 $Na_2HPO_4$ buffer was added. The buffer flowed through the column under its gravity. The column was then placed in a centrifuge and centrifuged for 2 min at 1000 g. Afterwards, a fresh collection tube replaced the old one and 1 ml of polysaccharide solution oxidised by sodium periodate was applied to the centrifugal column and centrifuged again at 1000 g for 2 min. The collected effluent from the column was the high activation activated polysaccharide solution.

2.3 Low Activation Degree Activation of Polysaccharides.

30 mg of sodium periodate was added to 10 mL of 10 mg/ml polysaccharide solution and mixed well. A centrifugal chromatography column containing 5 ml of Sephadex G 25 packing was taken and 10 ml of 50 mM $Na_2HPO_4$ buffer, pH=7.0, was added. The column was then placed in a centrifuge and centrifuged for 2 min at 1000 g. Afterwards a fresh collection tube replaced the old one and 1 ml of polysaccharide solution oxidised with sodium periodate was applied to the column and centrifuged again for 2 min at 1000 g. The collected effluent from the column was the low activation activated polysaccharide solution.

Example 3: Protein/Peptide Antigen Conjugated with Polysaccharide

The protein/peptide antigen used is the coronavirus spike protein receptor binding region and the polysaccharide is *Streptococcus pneumoniae* capsular polysaccharide or dextran. The specific components, amounts and volumes are shown in Table 1.

1. Coronavirus spike receptor protein buffer exchange: 5 mg of coronavirus spike receptor protein was taken and exchanged into 50 mM $Na_2HPO_4$ buffer, pH 7.0, using a 30,000 MW ultrafiltration tube, and the final concentration of the exchanged protein was required to be ≥10 mg/mL.

2. Coronavirus spike receptor protein and polysaccharide conjugation: 3 mg of coronavirus spike receptor protein was added to activated *Streptococcus pneumoniae* capsular polysaccharide or dextran according to Table 1 and supplemented with 50 mM $Na_2HPO_4$ buffer, pH 7.0, in the final volume shown in Table 1. 10 mg/mL of sodium borohydride solution was added to the reaction solution (0.15 ml to 0.6 ml of reaction system and 0.375 ml to 1.5 ml of reaction system) and the reaction was carried out for 2 h at room temperature. The conjugate was then filtered aseptically through a 100,000 MW ultrafiltration tube with a 10-fold exchange of PBS buffer to a final ultrafiltration volume of less than 2 ml. 0.22 μm filters were used to filter the fixative samples aseptically and store them at 4° C.

3. Determination of the molecular weight of the conjugate using HPLC-MALLS. The results are shown in Table 1.

18

MERS-COV RBD-his (source: Beijing Sino Biological, Inc . . . , 40071-V08B1), other proteins were prepared by the inventors themselves.

Example 4. Protein/Peptide Antigen and Protein Carrier Conjugated with Polysaccharide The protein/peptide antigen used was SARS-COV-2 RBD, the coronavirus spike protein receptor binding region, the protein vector was CRM197, and the polysaccharide was capsular polysaccharide of *Streptococcus pneumoniae*. The specific composition, amount and volume were shown in Table 2.

CRM197 is a variant of diphtheria toxin (Geert J. Schenk, Efficient CRM197-mediated drug targeting to monocytes, *Journal of Controlled Release* 158 (2012) 139-147). The coronavirus spike protein receptor-binding region and CRM197 are co-conjugated with the capsular polysaccharide of *Streptococcus pneumoniae* serotype 14. The activation of the polysaccharide proceeded as in Example 2.2. 1.5 mg of polysaccharide, 2.7 mg of coronavirus spike protein receptor binding region protein, and 0.3 mg of CRM197 were taken and conjugated according to the same procedure as in Example 3. The reaction conditions of the conjugates and the molecular weights of their products are shown in Table 2.

TABLE 1

Reaction conditions of several conjugates and molecular weights of their products

| Conjugate | Antigen | Poly-saccharide | Activation degree of poly-saccharide | Amount of antigen (mg) | Molecular weight of poly-saccharide (kDa) | Poly-saccharide (mg) | Total volume (ml) | 5M sodium cyanoboro-hydride (μl) | Molecular weight of conjugate (kDa) |
|---|---|---|---|---|---|---|---|---|---|
| SARS-COV-2 RBD-mFc - PS14 Conj-1 | SARS-COV-2 RBD -mFc | PS14 | low | 3 | 322 | 0.3 | 0.6 | 3.6 | 908 |
| SARS-COV-2 RBD-mFc - PS14 Conj-2 | SARS-COV-2 RBD -mFc | PS14 | low | 3 | 322 | 0.6 | 0.6 | 3.6 | 907.7 |
| SARS-COV-2 RBD-mFc - PS14 Conj-3 | SARS-COV-2 RBD-mFc | PS14 | low | 3 | 526 | 1.5 | 1.5 | 9 | 1059 |
| SARS-COV-2 RBD-mFc - PS14 Conj-4 | SARS-COV-2 RBD-mFc | PS14 | low | 3 | 526 | 1.5 | 0.6 | 3.6 | 4449/ 1090 |
| SARS-COV-2 RBD-his -PS14 | SARS-COV-2 RBD-his | PS14 | high | 3 | 355 | 1.5 | 0.6 | 3.6 | 4716 13340/ |
| SARS-COV-2 RBD- mFc - PS14 | SARS-COV-2 RBD-mFC | PS14 | high | 3 | 355 | 1.5 | 0.6 | 3.6 | 2328/ 479* |
| SARS-COV-2 RBD-hi s-PS7F | SARS-COV-2 RBD-his | PS7F | high | 3 | 9 | 1.5 | 0.6 | 3.6 | 921.4 |
| SARS-COV-2 RBD-his - dextran | SARS-COV-2 RBD-his | Dextran | high | 3 | 257 | 1.5 | 0.6 | 3.6 | 9524 |
| MERS-COV RBD-his -PS14 | MERS-COV RBD-his | PS14 | high | 3 | 154 | 1.5 | 0.6 | 3.6 | 1300 |

*denotes molecular weight of the three peaks of the affixation determined by HPLC-MALLS

TABLE 2

| | | | | | Carrier protein (mg) | Molecular weight of poly-saccharide (kDa) | Amount of poly-saccharide (mg) | Total volume (ml) | 5M sodium cyanoboro-hydride (μl) | Molecular weight of conjugate (kDa) |
|---|---|---|---|---|---|---|---|---|---|---|
| Conjugate | Antigen | Poly-saccharide | Activation degree | Antigen (mg) | | | | | | |
| (SARS-COV-2 RBD-his+CRM197)-PS14 | SARS-COV-2 RBD-his | PS14 | high | 2.7 | 0.3 | 355 | 1.5 | 0.6 | 3.6 | 3340 |
| (SARS-COV-2 RBD- mFC+ CRM197)-PS14 | SARS-COV-2 RBD-mFc | PS14 | high | 2.7 | 0.3 | 355 | 1.5 | 0.6 | 3.6 | 12740/ 2163/ 435* |

Reaction conditions of SARS-COV-2 RBD and CRM197 co-conjugates and the molecular weights of their products

Example 5. Immunogenicity of Coronavirus Spike Protein Receptor-Binding Region-Polysaccharide Conjugates The coronavirus spike protein receptor binding region-polysaccharide conjugates used were shown in Tables 3-6.

5.1 Preparation of the Immunogenic Compositions

Immunogenic compositions were prepared using the coronavirus spike protein receptor binding region protein or the conjugates prepared in Examples 3 or 4 as antigens.

5.1.1 Preparation of MF59 Adjuvant

Prepare 200 ml of 10 mM sodium citrate solution (pH 6.5 adjusted by HCl) and add 1 ml of Tween 80 (Nanjing Well Pharmaceutical co., LTD) and mix well to dissolve. Take 10 ml of squalene (Merck) and add 1 ml of Span 85 (Zhaoqing Chaoneng Industrial Co., Ltd.) and mix well to dissolve. The two previous solutions were mixed and homogenised 3 times using a high pressure homogeniser (AH-PILOTATS) set at 800 bar to obtain a homogeneous emulsion as MF59 adjuvant.

5.1.2 Preparation of MF59 Adjuvant Containing Monophosphatidyl Lipid A (MPL)

10 mg of MPL (MERCK L6895) was dispersed in 10 ml of sodium citrate buffer (10 mM, pH 6.5). Another 4 ml of MF59 adjuvant was added to 1 ml of MPL dispersion and mixed to obtain MF59 adjuvant containing MPL.

5.1.3 Preparation of Aluminium Adjuvant Immunogenic Compositions

The antigen was diluted to 0.02 mg/ml or 0.06 mg/ml (in terms of peptide/protein, hereinafter) with PBS and the aluminium adjuvant (Beijing Nuoning Biotechnology Co., Ltd.) was diluted to 1 mg/ml with PBS. The diluted antigen and aluminium adjuvant were mixed in equal volumes. The protein concentration of the antigen in this immunogenic composition was 0.01 mg/ml or 0.03 mg/ml respectively.

5.1.4 Preparation of MF59 Adjuvant Immunogenic Compositions

The antigen was diluted with PBS to 0.02 mg/ml or 0.06 mg/ml, respectively, and the diluted antigen was mixed with an equal volume of MF59 adjuvant. The protein concentration of the antigen in this immune composition was 0.01 mg/ml or 0.03 mg/ml, respectively.

5.1.5 Preparation of MF59 Adjuvant Immunogenic Compositions Containing MPL

The antigen was diluted with PBS to 0.02 mg/ml or 0.06 mg/ml, respectively, and the diluted antigen was mixed with an equal volume of MF59 adjuvant containing MPL. The protein concentration of the antigen in this immune composition was 0.01 mg/ml or 0.03 mg/ml, respectively.

5.1.6 Preparation of the MF59 and Aluminium Adjuvant Mixed Adjuvant Immunogenic Compositions 1.5 ml of aluminium adjuvant and 1.5 ml of MF59 adjuvant were mixed and then 0.18 ml of antigen at a concentration of 1 mg/ml was added. The protein concentration of the antigen in this immune composition was 0.03 mg/ml.

5.2 Immunized Mice.

Mice were selected from 4-6 week old Balb/c mice and were injected intraperitoneally with 0.1 ml of the immune composition at a concentration of 0.01 mg/ml or 0.03 mg/ml as described in Example 5.1 and immunised on day 14 and day 28 respectively. Blood was taken from the orbits on days 7, 21 and 35 to determine serum antibody titres and neutralisation titres.

5.3 Assay of Serum Potency 5.3.1 Assay of Serum Potency when the Antigen is SARS-COV-2 RBD or its Fusion Protein A concentration of 5 μg/mL of SARS-COV-2 RBD-mFc protein (SinoCelltech Ltd., full text) was used to coat a 96-well plate at 100 μl/well for 2 hours at room temperature, and the plate was washed and closed with 2% BSA for 1 hour at room temperature, using CD155(D1)-mFc (SinoCelltech Ltd., full text) as an irrelevant control with the same label. The sera to be tested (prepared in Example 5.2) were diluted to different dilutions (the exact dilutions varied depending on the time set for immunological collection, e.g. 1000×, 8000×, 16000×, 32000× dilutions) using PBS containing 0.1% bovine serum albumin (BSA), and mouse sera immunised with SARS-COV-2 RBD-mFc were used as positive, the mouse serum of unrelated immune target (anti-CD70 serum, Beijing Sino Biological, Inc.) was used as negative control, the serum to be tested and goat anti-mouse IgG F(ab)2/HRP (Beijing Sino Biological, Inc.) detection secondary antibody at different dilutions were added at the same time, 100 μl/well each. The OD450 at a certain dilution level indicates the antibody titer.

5.3.2 Assay of Serum Potency when the Antigen is MERS-COV RBD or its Fusion Protein In the MERS-COV RBD-his immune serum assay, the plate is coated with MERS-COV RBD-his (Beijing Sino Biological, Inc., 40071-V08B1) without a positive or negative control. Other steps are the same as 5.3.1.

5.3.3 Serum Potency Assay Results

The results of the serum potency assay are shown in Tables 3-5 and FIGS. 1-4.

The potency of the aluminium adjuvant immunisation combination is shown in Table 3 for mice immunised for 35 days at a serum of 8000× dilutions.

TABLE 3

Serum potency of the aluminium adjuvant immunogenic
compositions in mice at 35 days (results at 35 days of immunisation)

| Antigen | Immunizing dose (μg) | 8,000x dilution of the serum (OD$_{450}$) |
|---|---|---|
| SARS-COV-2 RBD-mFc | 1 | 0.319 |
| SARS-COV-2 RBD-mFc | 3 | 0.591 |
| SARS-COV-2 RBD-mFc-PS14 Conj-1 | 3 | 0.609 |
| SARS-COV-2 RBD-mFc-PS14 Conj-2 | 1 | 1.232 |
| SARS-COV-2 RBD-mFc-PS14 Conj-2 | 3 | 0.844 |
| SARS-COV-2 RBD-mFc-PS14 Conj-3 | 3 | 1.348 |
| SARS-COV-2 RBD-mFc-PS14 Conj-4 | 1 | 1.384 |
| SARS-COV-2 RBD-mFc-PS14 Conj-4 | 3 | 0.950 |
| SARS-COV-2 RBD-his | 3 | 0.171 |
| SARS-COV-2 RBD-his-PS14 | 3 | 1.694 |
| SARS-COV-2 RBD-his-CRM197-PS14 | 3 | 1.403 |
| SARS-COV-2 RBD-mFc-PS14 | 3 | 1.224 |
| SARS-COV-2 RBD-mFc-CRM197-PS14 | 3 | 0.839 |

The potency results of the SARS-COV-2 RBD-his-PS14 aluminium/MF59/MF59-aluminium/MF59-MPL adjuvant immunogenic composition at Day 35 serum of 32,000× dilutions are shown in Table 4.

TABLE 4

Serum potency of the conjugate SARS-COV-2
RBD-his -PS14 when combinized with different adjuvants
(Day 35 immunization results, immunization dose 3 μg)

| Adjuvant | 32,000× dilution of the serum (OD$_{450}$) |
|---|---|
| Aluminium adjuvant | 0.423 |
| MF59 | 1.052 |
| MF59-aluminium | 1.114 |
| MF59-MPL | 1.111 |

The serum potency of the MF59 adjuvant immune composition in mice immunised at Day 21Day 21 at a serum of 8000× dilutions is shown in Table 5.

TABLE 5

Serum potency of MF59 adjuvant immunogenic compositions
(Day 21 of immunization, immunization dose 3 μg)

| Antigen | 8,000x dilution of the serum (OD$_{450}$) |
|---|---|
| SARS-COV-2 RBD-his-PS7F | 1.382 |
| SARS-COV-2 RBD-his-dextran | 1.040 |
| MERS-COV RBD-his-PS14 | 1.325 |

5.4 Assay of Neutralization Potency

The mouse serum sample obtained in Example 5.2 was empirically diluted a certain number of times (e.g., 500× dilution) and mixed with pseudovirus 2019-nCoV PSV (China Academy of Food and Drug Administration) in equal volume, use an otherwise the same sample without the serum as a positive control and an otherwise the same sample without the pseudovirus as a negative control, and incubated at 37° C. for 1 hour before simultaneous infestation with Vero E6 or 293 FT/ACE2 cells (SinoCelltech Ltd.). The cells were incubated at 37° C. with 5% CO$_2$ for about 20-28 hours after infection and the RLU values were measured on a microplate luminescence detector. According to Neutralisation inhibition %=(lg(positive RLU)−lg(sample RLU))/(lg(positive RLU)−lg(negative RLU))×100%, to calculate the neutralisation inhibition rate.

Figure 3:
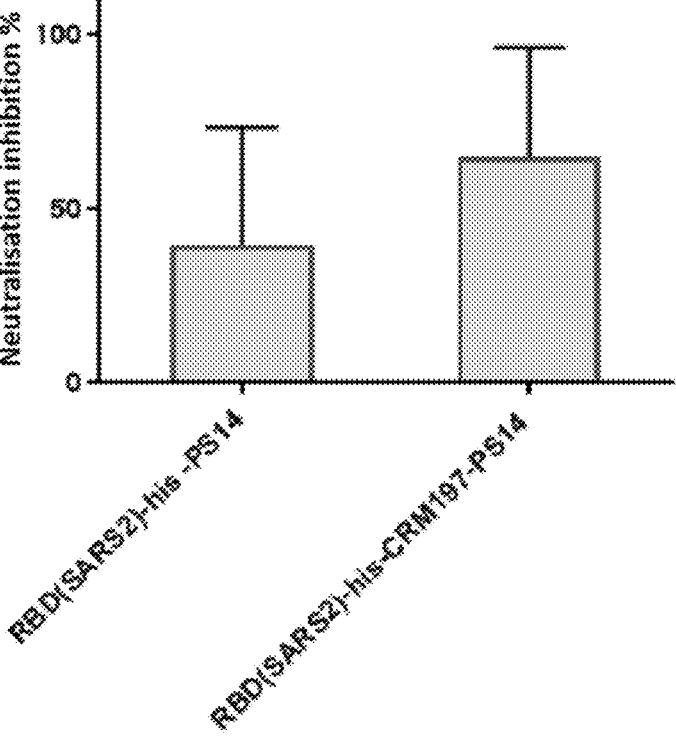
FIG. 3 depicts the SARS-COV-2 RBD protein-PS14 polysaccharide conjugate, and a comparison of the serum neutralizing activity of immune combinations of SARS-COV-2 RBD and CRM197 co-conjugated with PS14 as antigen in immunized mice at a serum dilution of 1500×, and an immunization dose of 3 μg/mouse.
Figure 4:
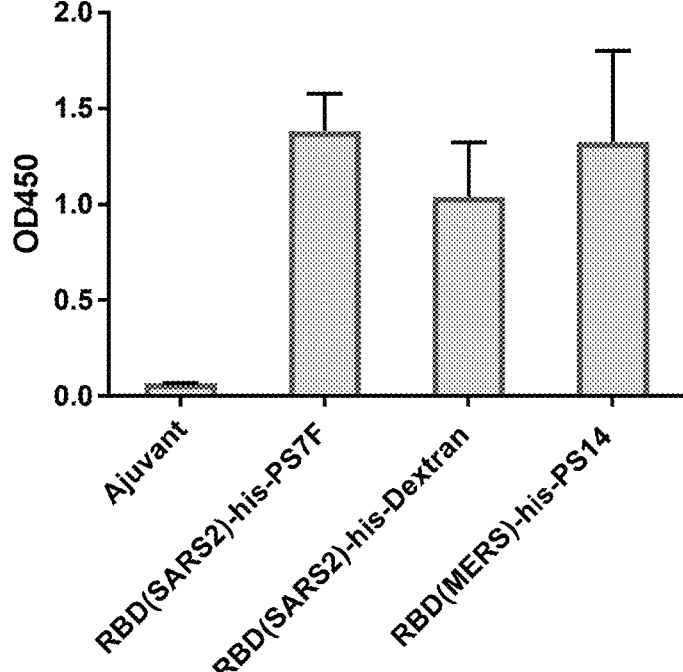
FIG. 4 depicts the immunological results of PS7F, PS14 and dextran as the conjugate agent for the conjugate.

The results of the neutralisation potency of the sera from mice immunised with the different immunogenic compositions are shown in Table 6 and FIG. 3.

TABLE 6

Neutralisation potency of immunogenic compositions
(day 35 results, immunisation dose 3 μg)

| Antigen | Neutralisation inhibition at 500x dilution of the serum (%) | Neutralisation inhibition at 1,500x dilution of the serum (%) |
|---|---|---|
| SARS-COV-2 RBD-mFc | 36.7 | — |
| SARS-COV-2 RBD-mFc-PS14 Conj-1 | 56.1 | — |
| SARS-COV-2 RBD-mFc-PS14 Conj-2 | 64.7 | — |
| SARS-COV-2 RBD-mFc-PS14 Conj-3 | 93.0 | — |
| SARS-COV-2 RBD-mFc-PS14 Conj-4 | 90.6 | — |
| SARS-COV-2 RBD-his | 16.2 | — |
| SARS-COV-2 RBD-his-PS14 | 90.3 | 40 |
| SARS-COV-2 RBD-his-CRM197-PS14 | 100 | 65 |
| SARS-COV-2 RBD-mFc-PS14 | 59.8 | 18 |
| SARS-COV-2 RBD-mFc-CRM197-PS14 | 59.3 | 12.75 |

Example 6. Immunogenicity Enhancement of Several Viral Antigens by Polysaccharides Several viral antigens, as shown in Table 7 (all from Beijing Sino Biological, Inc.), were selected and conjugated with PS14 polysaccharide in the following steps.

*Streptococcus pneumoniae* serotype 14 (PS14) was prepared according to Example 1 and activated according to the steps of Example 2.2, where the amount of sodium periodate added was adjusted according to Table 8. PS14 was conjugated to the carrier protein CRM197 according to the steps of Example 3, with the ratio of protein to polysaccharide for conjugation as shown in Table 8. Prepare the aluminium-containing adjuvant immunogenic compositions according to Example 5.1.3. Mice were immunised according to Example 5.2 at a dose of 3 μg antigen per mouse.

The immune serum potency was assayed using the corresponding antigen coating without positive and negative controls and the procedure was exactly the same as in 5.3.1.

The immunoserum potencies of the various antigen conjugates are shown in Table 8. It can be seen that for most antigens there is a significant increase in immunogenicity after conjugation with polysaccharides.

TABLE 7

Names, Catalog Numbers and corresponding abbreviations of several viral antigens

| Antigens | Cat no(Sinobiological) | SEQ ID NO | Abbreviation |
|---|---|---|---|
| Human respiratory syncytial virus glycoprotein G (His Tag) | 11070-V08B2 | 12 | RSV-gpG-his |

TABLE 7-continued

Names, Catalog Numbers and corresponding abbreviations of several viral antigens

| Antigens | Cat no(Sinobiological) | SEQ ID NO | Abbreviation |
|---|---|---|---|
| Hepatitis C virus Envelope Glycoprotein E1 | 40374-V07H | 13 | HCV-E1-his |
| Hepatitis C virus Envelope E2 Protein (His Tag) | 40375-V08H | 14 | HCV-E2-his |
| Influenza B Hemagglutinin Protein (HA1 Subunit) (His Tag) | 40016-V08H1 | 15 | flu-B-HA1-his |
| Influenza A H5N1 Hemagglutinin (His Tag) | 11048-V08H1 | 16 | H5N1-HA-his |
| Ebola virus Glycoprotein (Receptor Binding Domain, Fc Tag) | 40368-V02H | 17 | Ebola-GP-Fc |
| Ebola virus Glycoprotein GP1 (His Tag) | 40094-V08H2 | 18 | Ebola-GP1-his |
| Zika virus Envelope protein (Domain III, Fc Tag) | 40543-V02H | 19 | ZIKV-E-Fc |

TABLE 8

Conjugation condition and immunoserum potency of several viral antigen-polysaccharide conjugates

| Code No. | Conjugated polysaccharide | Activation | | Conjugation | | Serum potency (1,000× dilution of the serum) OD450 |
|---|---|---|---|---|---|---|
| | | Polysaccharide mg | Sodium periodate mg | Antigen mg | Poly-saccharide mg | OD450 (1000) |
| HCV-E1 | PS14 | 100 | 100 | 3 | 1.5 | 0.280 |
| flu-B-HA1 | PS14 | 100 | 100 | 3 | 1.5 | 0.810 |
| H5N1-HA | PS14 | 100 | 100 | 3 | 1.5 | 3.514 |
| Ebola-GP-Fc | PS14 | 100 | 100 | 3 | 1.5 | 2.259 |
| Ebola-GP1 | PS14 | 100 | 100 | 3 | 1.5 | 0.439 |
| ZIKV-E-Fc | PS14 | 100 | 100 | 3 | 1.5 | 3.520 |
| HCV-E2 | PS14 | 100 | 100 | 3 | 6 | 0.220 |
| | PS14 | 100 | 100 | 3 | 3 | 0.312 |
| | PS14 | 100 | 100 | 3 | 1.5 | 0.301 |
| | PS14 | 100 | 100 | 3 | 0.6 | 0.242 |
| | PS14 | 100 | 100 | 3 | 0.3 | 0.756 |
| RSV-gpG | PS14 | 100 | 200 | 3 | 1.5 | 1.907 |
| | PS14 | 100 | 100 | 3 | 1.5 | 2.017 |
| | PS14 | 100 | 50 | 3 | 1.5 | 2.060 |
| RSV-gpG | — | — | — | — | — | 0.629 |
| HCV-E1 | — | — | — | — | — | 0.284 |
| HCV-E2 | — | — | — | — | — | 0.298 |
| flu-B-HA1 | — | — | — | — | — | 0.052 |
| H5N1-HA | — | — | — | — | — | 1.705 |
| Ebola-GP-Fc | — | — | — | — | — | 2.688 |
| Ebola-GP1 | — | — | — | — | — | 0.207 |
| ZIKV-E-Fc | — | — | — | — | — | 2.887 |

The antigens used in Table 8 are documented in Table 7, where His-tag is not shown.

According to the above data, the immunogenicity of the protein antigens was significantly increased when they were conjugated with *Streptococcus pneumoniae* capsular polysaccharide. Under aluminium adjuvant conditions, the antibody potency of the immune serum of the conjugate reached up to 2.3 times the original potency. The neutralising activity of the conjugate was also substantially higher than that of the corresponding proteins. Compared to aluminium adjuvant, MF59 adjuvant, MF59 mixed with aluminium adjuvant and MF59 adjuvant containing MPL adjuvant all further improve the immune effect of the conjugate. The immunological effect was similar when using *Streptococcus pneumoniae* serotype 14 capsular polysaccharide, *Streptococcus pneumoniae* serotype 7F capsular polysaccharide and dextran as conjugate.

Sequence Listing
SARS-COV-2 RBD

SEQ ID NO: 1

RVQPTESIVRFPNITNLCPFGEVFNATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGVGYQPYRVVVLSFELLHAPATVC

GPKKSTNLVKNKCVNF

-continued

SARS-COV-2RBD-his

SEQ ID NO: 2

RVQPTESIVRFPNITNLCPFGEVFNATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGVGYQPYRVVVLSFELLHAPATVC

GPKKSTNLVKNKCVNFAHHHHHHHHHH

SARS-COV-2 RBD-mFc

SEQ ID NO: 3

RVQPTESIVRFPNITNLCPFGEVFNATRFASVYAWNRKRISNCVADYSVLYNSASFSTFKCYGVSPT

KLNDLCFTNVYADSFVIRGDEVRQIAPGQTGKIADYNYKLPDDFTGCVIAWNSNNLDSKVGGNYNYLYR

LFRKSNLKPFERDISTEIYQAGSTPCNGVEGFNCYFPLQSYGFQPTNGVGYQPYRVVVLSFELLHAPATVC

GPKKSTNLVKNKCVNFADDDDKAVPRDSGCKPCICTVPEVSSVFIFPPKPKDVLTITLTPKVTCVVVDISK

DDPEVQFSWFVDDVEVHTAQTQPREEQFNSTFRSVSELPIMHQDWLNGKEFKCRVNSAAFPAPIEKTISK

TKGRPKAPQVYTIPPPKEQMAKDKVSLTCMITDFFPEDITVEWQWNGQPAENYKNTQPIMDTDGSYFVY

SKLNVQKSNWEAGNTFTCSVLHEGLHNHHTEKSLSHSPGK

RSV-gpG

SEQ ID NO: 4

NHKVTSTTTIIQDATSQIKNTTPTYLTQSPQLGISPSNPSEITSQITTILASTTPGVKSTLQSTTVGTKN

TTTTQAQPSKPTTKQRQNKPPSKPNNDFHFEVFNFVPCSICSNNPTCWAICKRIPNKKPGKKTTTKPTEEP

TFKTAKEDPKPQTTGSGEVPTTKPTGEPTINTTKTNITTTLLTSNTTRNPELTSQMETFHSTSSEGNPSPSQV

SITSEYLSQPSSPPNTPR

HCV-E1

SEQ ID NO: 5

ALEVLFQGPYEVRNVSGIYHVTNDCSNSSIVYEAADVIMHTPGCVPCVREGNSSRCWVALTPTLA

ARNASVPTTTIRRHVDLLVGTAAFCSAMYVGDLCGSIFLVSQLFTFSPRRHETVQDCNCSIYPGHVSGHR

MAWDMMMNWSPTTALVVSQLLRI

HCV-E2

SEQ ID NO: 6

ETHTTGRVAGHTTSGFTSLFSSGASQKIQLVNINGSWHINRTALNCNDSLQTGFFAALFYAHKFNS

SGCPERMASCRPIDWFAQGWGPITYTKPNSSDQRPYCWHYAPRPCGVVPASQVCGPVYCFTPSPVVVGT

TDRSGVPTYSWGENETDMMLLNNTRPPQGNWFGCTWMNSTGFTKTCGGPPCNIGGVGNRTLICPTDCF

RKHPEATYTKCGSGPWLTPRCLVDYPYRLWHYPCTLNFSIFKVRMYVGGVEHRLNAACNWTRGERCNL

EDRDRSE flu-B-HA1

SEQ ID NO: 7

DRICTGITSSNSPHVVKTATQGEVNVTGVIPLTTTPTKSHFANLKGTETRGKLCPKCLNCTDLDVAL

GRPKCTGKIPSARVSILHEVRPVTSGCFPIMHDRTKIRQLPNLLRGYEHIRLSTHNVINAENAPGGPYKIGT

SGSCPNITNGNGFFATMAWAVPKNDKNKTATNPLTIEVPYICTEGEDQITVWGFHSDNETQMAKLYGDS

KPQKFTSSANGVTTHYVSQIGGFPNQTEDGGLPQSGRIVVDYMVQKSGKTGTITYQRGILLPQKVWCAS

GRSKVIKGSLPLIGEADCLHEKYGGLNKSKPYYTGEHAKAIGNCPIWVKTPLKLANGTKYRPPAKLLKER

H5N1-HA

SEQ ID NO: 8

DQICIGYHANNSTEQVDTIMEKNVTVTHAQDILEKTHNGKLCDLDGVKPLILRDCSVAGWLLGNP

MCDEFINVPEWSYIVEKANPANDLCYPGNFNDYEELKHLLSRINHFEKIQIIPKSSWSDHEASSGVSSACP

YQGTPSFFRNVVWLIKKNNTYPTIKRSYNNTNQEDLLILWGIHHSNDAAEQTKLYQNPTTYISVGTSTLN

QRLVPKIATRSKVNGQSGRMDFFWTILKPNDAINFESNGNFIAPEYAYKIVKKGDSAIVKSEVEYGNCNT

KCQTPIGAINSSMPFHNIHPLTIGECPKYVKSNKLVLATGLRNSPLTETRGLFGAIAGFIEGGWQGMVDG

-continued

WYGYHHSNEQGSGYAADKESTQKAIDGVTNKVNSIIDKMNTQFEAVGREFNNLERRIENLNKKMEDGF

LDVWTYNAELLVLMENERTLDFHDSNVKNLYDKVRLQLRDNAKELGNGCFEFYHKCDNECMESVRNG

TYDYPQYSEEARLKREEISGVKLESIGTYQ

Ebola-GP

SEQ ID NO: 9

IPLGVVHNNTLQVSDIDKLVCRDKLSSTSQLKSVGLNLEGNGVATDVPTATKRWGFRAGVPPKVV

NYEAGEWAENCYNLDIKKADGSECLPEAPEGVRGFPRCRYVHKVSGTGPCPEGYAFHKEGAFFLYDRL

ASTIIYRSTTFSEGVVAFLILPETKKDFFQSPPLHEPANMTTDPSSYYHTVTLNYVADNFGTNMTNFLFQV

DHLTYVQLEPRFTPQFLVQLNETIYTNGRRSNTTGTLIWKVNPTVDTGVGEWAFWENKKNFTKTLSSEE

LSV

Ebola-GP1

SEQ ID NO: 10

MPLGVVTNSTLEVTEIDQLVCKDHLASTDQLKSVGLNLEGSGVSTDIPSATKRWGFRSGVPPKVVS

YEAGEWAENCYNLEIKKPDGSECLPPPPDGVRGFPRCRYVHKAQGTGPCPGDYAFHKDGAFFLYDRLAS

TVIYRGVNFAEGVIAFLILAKPKETFLQSPPIREAVNYTENTSSYYATSYLEYEIENFGAQHSTTLFKIDNNT

FVRLDRPHTPQFLFQLNDTIHLHQQLSNTTGRLIWTLDANINADIGEWAFWENKKNLSEQLRGEELSFEA

LSLNETEDDDAASSRITKGRISDRATRKYSDLVPKNSPGMVPLHIPEGETTLPSQNSTEGRRVGVNTQETI

TETAATIIGTNGNHMQISTIGIRPSSSQIPSSSPTTAPSPEAQTPTTHTSGPSVMATEEPTTPPGSSPGPTTEAP

TLTTPENITTAVKTVLPQESTSNGLITSTVTGILGSLGLRKRSRR

ZIKV-E

SEQ ID NO: 11

VSYSLCTAAFTFTKIPAETLHGTVTVEVQYAGTDGPCKVPAQMAVDMQTLTPVGRLITANPVITES

TENSKMMLELDPPFGDSYIVIGVGEKKITHHWHRSGSTIGK

RSV-gpG-his

SEQ ID NO: 12

NHKVTSTTTIIQDATSQIKNTTPTYLTQSPQLGISPSNPSEITSQITTILASTTPGVKSTLQSTTVGTKN

TTTTQAQPSKPTTKQRQNKPPSKPNNDFHFEVFNFVPCSICSNNPTCWAICKRIPNKKPGKKTTTKPTEEP

TFKTAKEDPKPQTTGSGEVPTTKPTGEPTINTTKTNITTTLLTSNTTRNPELTSQMETFHSTSSEGNPSPSQV

SITSEYLSQPSSPPNTPRAHHHHHHHHHH

HCV-E1-his

SEQ ID NO: 13

HHHHHHHHHHALEVLFQGPYEVRNVSGIYHVTNDCSNSSIVYEAADVIMHTPGCVPCVREGNSSR

CWVALTPTLAARNASVPTTTIRRHVDLLVGTAAFCSAMYVGDLCGSIFLVSQLFTFSPRRHETVQDCNCS

IYPGHVSGHRMAWDMMMNWSPTTALVVSQLLRI

HCV-E2-his

SEQ ID NO: 14

ETHTTGRVAGHTTSGFTSLFSSGASQKIQLVNINGSWHINRTALNCNDSLQTGFFAALFYAHKFNS

SGCPERMASCRPIDWFAQGWGPITYTKPNSSDQRPYCWHYAPRPCGVVPASQVCGPVYCFTPSPVVVGT

TDRSGVPTYSWGENETDMMLLNNTRPPQGNWFGCTWMNSTGFTKTCGGPPCNIGGVGNRTLICPTDCF

RKHPEATYTKCGSGPWLTPRCLVDYPYRLWHYPCTLNFSIFKVRMYVGGVEHRLNAACNWTRGERCNL

EDRDRSEAHHHHHHHHHH flu-B-HA1-his

SEQ ID NO: 15

DRICTGITSSNSPHVVKTATQGEVNVTGVIPLTTTPTKSHFANLKGTETRGKLCPKCLNCTDLDVAL

GRPKCTGKIPSARVSILHEVRPVTSGCFPIMHDRTKIRQLPNLLRGYEHIRLSTHNVINAENAPGGPYKIGT

SGSCPNITNGNGFFATMAWAVPKNDKNKTATNPLTIEVPYICTEGEDQITVWGFHSDNETQMAKLYGDS

KPQKFTSSANGVTTHYVSQIGGFPNQTEDGGLPQSGRIVVDYMVQKSGKTGTITYQRGILLPQKVWCAS

-continued

GRSKVIKGSLPLIGEADCLHEKYGGLNKSKPYYTGEHAKAIGNCPIWVKTPLKLANGTKYRPPAKLLKER

AHHHHHHHHHH

H5N1-HA-his

SEQ ID NO: 16

DQICIGYHANNSTEQVDTIMEKNVTVTHAQDILEKTHNGKLCDLDGVKPLILRDCSVAGWLLGNP

MCDEFINVPEWSYIVEKANPANDLCYPGNFNDYEELKHLLSRINHFEKIQIIPKSSWSDHEASSGVSSACP

YQGTPSFFRNVVWLIKKNNTYPTIKRSYNNTNQEDLLILWGIHHSNDAAEQTKLYQNPTTYISVGTSTLN

QRLVPKIATRSKVNGQSGRMDFFWTILKPNDAINFESNGNFIAPEYAYKIVKKGDSAIVKSEVEYGNCNT

KCQTPIGAINSSMPFHNIHPLTIGECPKYVKSNKLVLATGLRNSPLTETRGLFGAIAGFIEGGWQGMVDG

WYGYHHSNEQGSGYAADKESTQKAIDGVTNKVNSIIDKMNTQFEAVGREFNNLERRIENLNKKMEDGF

LDVWTYNAELLVLMENERTLDFHDSNVKNLYDKVRLQLRDNAKELGNGCFEFYHKCDNECMESVRNG

TYDYPQYSEEARLKREEISGVKLESIGTYQAHHHHHHHHHH

Ebola-GP-Fc

SEQ ID NO: 17

IPLGVVHNNTLQVSDIDKLVCRDKLSSTSQLKSVGLNLEGNGVATDVPTATKRWGFRAGVPPKVV

NYEAGEWAENCYNLDIKKADGSECLPEAPEGVRGFPRCRYVHKVSGTGPCPEGYAFHKEGAFFLYDRL

ASTIIYRSTTFSEGVVAFLILPETKKDFFQSPPLHEPANMTTDPSSYYHTVTLNYVADNFGTNMTNFLFQV

DHLTYVQLEPRFTPQFLVQLNETIYTNGRRSNTTGTLIWKVNPTVDTGVGEWAFWENKKNFTKTLSSEE

LSVADDDDKEPKSSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Ebola-GP1-his

SEQ ID NO: 18

MPLGVVTNSTLEVTEIDQLVCKDHLASTDQLKSVGLNLEGSGVSTDIPSATKRWGFRSGVPPKVVS

YEAGEWAENCYNLEIKKPDGSECLPPPPDGVRGFPRCRYVHKAQGTGPCPGDYAFHKDGAFFLYDRLAS

TVIYRGVNFAEGVIAFLILAKPKETFLQSPPIREAVNYTENTSSYYATSYLEYEIENFGAQHSTTLFKIDNNT

FVRLDRPHTPQFLFQLNDTIHLHQQLSNTTGRLIWTLDANINADIGEWAFWENKKNLSEQLRGEELSFEA

LSLNETEDDDAASSRITKGRISDRATRKYSDLVPKNSPGMVPLHIPEGETTLPSQNSTEGRRVGVNTQETI

TETAATIIGTNGNHMQISTIGIRPSSSQIPSSSPTTAPSPEAQTPTTHTSGPSVMATEEPTTPPGSSPGPTTEAP

TLTTPENITTAVKTVLPQESTSNGLITST VTGILGSLGLRKRSRRAHHHHHHHHHH

ZIKV-E-Fc

SEQ ID NO: 19

VSYSLCTAAFTFTKIPAETLHGTVTVEVQYAGTDGPCKVPAQMAVDMQTLTPVGRLITANPVITES

TENSKMMLELDPPFGDSYIVIGVGEKKITHHWHRSGSTIGKADDDDKEPKSSDKTHTCPPCPAPELLGGP

SVFLFPPKPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSVMHEALHNHYTQKSLSLSP

GK

The invention claimed is:

1. A method for improving the immunogenicity of a protein/peptide antigen, comprising forming a glyco-protein/peptide antigen conjugate by conjugating the protein/peptide antigen with a saccharide,
    wherein the saccharide is capsular polysaccharide of *Streptococcus pneumonia*,
    wherein the protein/peptide antigen is a virus pathogen-associated protein/peptide antigen selected from human respiratory syncytial virus glycoprotein G (RSV-gpG), hepatitis C virus envelope glycoprotein E1 protein (ECV-E1), hepatitis C virus envelope E2 protein (HCV-E2), influenza B hemagglutinin protein (FLU-B-HA1), influenza A H5N1 hemagglutinin (H5N1-HA), ebola virus glycoprotein (Ebola-GP), ebola virus glycoprotein GP1 (Ebola-GP1), zika virus envelope protein (ZIKV-E), and/or coronavirus spike protein.

2. The method as claimed in claim 1, wherein the saccharide is
    capsular polysaccharide of *Streptococcus pneumoniae* serotype 14, 6B or 7F.

3. The method as claimed in claim 1, wherein the protein/peptide antigen is a protein/peptide comprising
    viral antigen of
    coronavirus spike protein receptor binding region RBD.

4. The method as claimed in claim 3, wherein the coronavirus is SARS-COV-2 or Middle East respiratory syndrome coronavirus.

5. The method as claimed in claim 3, wherein the protein/peptide antigen is a fusion protein
    which is SARS-COV-2 RBD-mFc; SARS-COV-2 RBD-his; or MERS-COV RBD-his; and
    the Fc fragment is a human or murine IgG Fc fragment.

6. The method as claimed in claim 4, wherein the protein/peptide antigen comprises the sequence as set forth as any one of SEQ ID NO:1, SEQ ID NO: 2 or SEQ ID NO:3.

7. The method as claimed in claim 1, wherein the molecular weight of the conjugate is 400-14000 KDa.

8. The method as claimed in claim 1, wherein the protein/peptide antigen is a fusion protein
    which is RSV-gpG-his.

9. The method as claimed in claim 1, wherein the protein/peptide antigen comprises the sequence as set forth as SEQ ID NO:4 or SEQ ID NO:12.

10. The method as claimed in claim 1, wherein the protein/peptide antigen is a fusion protein
    which is Flu-B-HA1-his or H5N1-HA-his.

11. The method as claimed in claim 1, wherein the protein/peptide antigen comprises the sequence as set forth as any one of SEQ ID NO:7, SEQ ID NO: 15, SEQ ID NO: 8 or SEQ ID NO: 16.

12. The method as claimed in claim 1, wherein the protein/peptide antigen is a fusion protein
    which is Ebola-GP-Fc or Ebola-GP1-his;
    wherein the Fc is a human or murine IgG Fc fragment.

13. The method as claimed in claim 1, wherein the protein/peptide antigen comprises the sequence as set forth as any one of SEQ ID NO: 9, SEQ ID NO: 17, SEQ ID NO: 10 or SEQ ID NO: 18.

14. The method as claimed in claim 1, wherein the protein/peptide antigen is a fusion protein
    which is ZIKV-E-Fc; wherein
    Fc is a human or murine IgG Fc fragment; or
    the fusion protein is HCV-E2-his and/or HCV-E1-his.

15. The method as claimed in claim 1, wherein the protein/peptide antigen comprises the sequence as set forth as any one of SEQ ID NO:11, SEQ ID NO: 19, SEQ ID NO: 6, SEQ ID NO:14, SEQ ID NO:5 or SEQ ID NO: 13.

16. The method as claimed in claim 1, wherein the glyco-protein/peptide antigen is further conjugated with a protein carrier.

17. The method as claimed in claim 16, wherein the protein carrier is a tetanus toxoid, a tetanus toxoid fragment C, a tetanus toxoid non-toxic mutant, a diphtheria toxoid, CRM197, or other non-toxic mutants of diphtheria toxoid.

18. A glyco-protein/peptide antigen conjugate with a saccharide increased immunogenicity compared to an unconjugated protein/peptide antigen;

wherein the saccharide is capsular polysaccharide of *Streptococcus pneumonia,* wherein the protein/peptide antigen is a virus pathogen-associated protein/peptide antigen selected from human respiratory syncytial virus glycoprotein G (RSV-gpG), hepatitis C virus envelope glycoprotein E1 protein (ECV-E1), hepatitis C virus envelope E2 protein (HCV-E2), influenza B hemagglutinin protein (FLU-B-HA1), influenza A H5N1 hemagglutinin (H5N1-HA), ebola virus glycoprotein (Ebola-GP), ebola virus glycoprotein GP1 (Ebola-GP1), zika virus envelope protein (ZIKV-E), and/or coronavirus spike protein.

19. The conjugate as claimed in claim 18, wherein the saccharide is capsular polysaccharide of *Streptococcus pneumoniae* serotype 14, 6B or 7F.

20. The conjugate as claimed in claim 18, wherein the protein/peptide antigen is a protein/peptide comprising viral antigens of the coronavirus spike protein receptor binding region RBD.

21. The conjugate as claimed in claim 20, wherein the coronavirus is SARS-CoV-2 or Middle East respiratory syndrome coronavirus.

22. The conjugate as claimed in claim 20, wherein the protein/peptide antigen is a fusion protein which is SARS-COV-2 RBD-mFc; SARS-COV-2 RBD-his; or MERS-COV RBD-his; and the Fc fragment is a human or murine IgG Fc fragment.

23. The conjugate as claimed in claim 21, wherein the protein/peptide antigen comprises the sequence as set forth as any one of SEQ ID NO:1, SEQ ID NO: 2 or SEQ ID NO:3.

24. The conjugate as claimed in claim 18, wherein the protein/peptide antigen is a fusion protein which is RSV-gpG-his.

25. The conjugate as defined in claim 18, wherein the protein/peptide antigen comprises the sequence as set forth as SEQ ID NO: 4 or SEQ ID NO:12.

26. The conjugate as claimed in claim 18, wherein the protein/peptide antigen is a fusion protein which is Flu-B-HA1-his or H5N1-HA-his.

27. The conjugate as claimed in claim 18, wherein the protein/peptide antigen comprises the sequence as set forth as any one of SEQ ID NO:7, SEQ ID NO:15, SEQ ID NO:8, or SEQ ID NO: 16.

28. The conjugate as claimed in claim 18, wherein the protein/peptide antigen is a fusion protein which is Ebola-GP-Fc or Ebola-GP1-his; and wherein the Fc is a human or murine IgG Fc fragment.

29. The conjugate as claimed in claim 18, wherein the protein/peptide antigen comprises the sequence as set forth as any one of SEQ ID NO:9, SEQ ID NO: 17, SEQ ID NO: 10, or SEQ ID NO: 18.

30. The conjugate as claimed in claim 18, wherein the protein/peptide antigen is a fusion protein which is HCV-E2-his and/or HCV-E1-his.

31. The conjugate as claimed in claim 18, wherein the protein/peptide antigen comprises the sequence as set forth as any one of SEQ ID NO:11, SEQ ID NO: 19, SEQ ID NO: 6, SEQ ID NO:14, SEQ ID NO:5, or SEQ ID NO:13.

32. The glyco-protein/peptide antigen conjugate as claimed in claim 18, wherein the glyco-protein/peptide antigen is further conjugated to a protein carrier.

33. The glyco-protein/peptide antigen conjugate as claimed in claim 32, wherein the protein carrier is tetanus toxoid, tetanus toxoid fragment C, tetanus toxoid non-toxic mutant, diphtheria toxoid, CRM197, other non-toxic mutants of diphtheria toxoid.

34. An immunogenic composition comprising the glyco-protein/peptide antigen conjugate of claim 18, immune adjuvant and excipient.

35. The immunogenic composition as claimed in claim 34, the adjuvant selected from aluminium adjuvant, oil-in-water emulsion adjuvant, MF59, QS-21 and lipid mono-phosphate A.

36. A method of preventing or treating disease caused by a pathogen-associated protein/peptide antigen, the method comprising administering the glyco-protein/peptide antigen conjugate of claim 18 to a subject in need thereof.

37. A method of preventing or treating a disease caused by a pathogen-associated protein/peptide antigen, the method comprising preparing a vaccine or drug comprising the glyco-protein/peptide antigen conjugate of 18 and administering said vaccine or drug to a subject in need thereof.

38. A method of preventing or treating a disease caused by a pathogen-associated protein/peptide antigen, the method comprising administering the immunogenic composition of claim 34 to a subject in need thereof.

39. A method of preventing or treating a disease caused by a pathogen-associated protein/peptide antigen, the method comprising preparing a vaccine or drug comprising the immunogenic composition of claim 34, and administering said vaccine or drug to a subject in need thereof.

\* \* \* \* \*

SEQUENCE LISTING

<160> NUMBER OF SEQ ID NOS: 19

<210> SEQ ID NO 1
<211> LENGTH: 223
<212> TYPE: PRT

```
<213> ORGANISM: Artificial
<220> FEATURE:
<223> OTHER INFORMATION: The sequence is artifically synthesized.

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220

<210> SEQ ID NO 2
<211> LENGTH: 234
<212> TYPE: PRT
<213> ORGANISM: Artificial
<220> FEATURE:
<223> OTHER INFORMATION: The sequence is artificially synthesized.

<400> SEQUENCE: 2

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110
```

-continued

```
Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Ala
    210                 215                 220

His His His His His His His His His His
225                 230
```

```
<210> SEQ ID NO 3
<211> LENGTH: 457
<212> TYPE: PRT
<213> ORGANISM: Artificial
<220> FEATURE:
<223> OTHER INFORMATION: The sequence is artificially synthesized.

<400> SEQUENCE: 3
```

```
Arg Val Gln Pro Thr Glu Ser Ile Val Arg Phe Pro Asn Ile Thr Asn
1                   5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
            85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Ala
    210                 215                 220

Asp Asp Asp Asp Lys Ala Val Pro Arg Asp Ser Gly Cys Lys Pro Cys
225                 230                 235                 240
```

-continued

```
Ile Cys Thr Val Pro Glu Val Ser Ser Val Phe Ile Phe Pro Pro Lys
            245             250             255

Pro Lys Asp Val Leu Thr Ile Thr Leu Thr Pro Lys Val Thr Cys Val
            260             265             270

Val Val Asp Ile Ser Lys Asp Asp Pro Glu Val Gln Phe Ser Trp Phe
        275             280             285

Val Asp Asp Val Glu Val His Thr Ala Gln Thr Gln Pro Arg Glu Glu
    290             295             300

Gln Phe Asn Ser Thr Phe Arg Ser Val Ser Glu Leu Pro Ile Met His
305             310             315             320

Gln Asp Trp Leu Asn Gly Lys Glu Phe Lys Cys Arg Val Asn Ser Ala
            325             330             335

Ala Phe Pro Ala Pro Ile Glu Lys Thr Ile Ser Lys Thr Lys Gly Arg
            340             345             350

Pro Lys Ala Pro Gln Val Tyr Thr Ile Pro Pro Lys Glu Gln Met
            355             360             365

Ala Lys Asp Lys Val Ser Leu Thr Cys Met Ile Thr Asp Phe Phe Pro
    370             375             380

Glu Asp Ile Thr Val Glu Trp Gln Trp Asn Gly Gln Pro Ala Glu Asn
385             390             395             400

Tyr Lys Asn Thr Gln Pro Ile Met Asp Thr Asp Gly Ser Tyr Phe Val
            405             410             415

Tyr Ser Lys Leu Asn Val Gln Lys Ser Asn Trp Glu Ala Gly Asn Thr
            420             425             430

Phe Thr Cys Ser Val Leu His Glu Gly Leu His Asn His His Thr Glu
            435             440             445

Lys Ser Leu Ser His Ser Pro Gly Lys
    450             455
```

```
<210> SEQ ID NO 4
<211> LENGTH: 232
<212> TYPE: PRT
<213> ORGANISM: Artificial
<220> FEATURE:
<223> OTHER INFORMATION: The sequence is artificially synthesized.

<400> SEQUENCE: 4

Asn His Lys Val Thr Ser Thr Thr Thr Ile Ile Gln Asp Ala Thr Ser
1               5               10              15

Gln Ile Lys Asn Thr Thr Pro Thr Tyr Leu Thr Gln Ser Pro Gln Leu
            20              25              30

Gly Ile Ser Pro Ser Asn Pro Ser Glu Ile Thr Ser Gln Ile Thr Thr
            35              40              45

Ile Leu Ala Ser Thr Thr Pro Gly Val Lys Ser Thr Leu Gln Ser Thr
    50              55              60

Thr Val Gly Thr Lys Asn Thr Thr Thr Gln Ala Gln Pro Ser Lys
65              70              75              80

Pro Thr Thr Lys Gln Arg Gln Asn Lys Pro Pro Ser Lys Pro Asn Asn
            85              90              95

Asp Phe His Phe Glu Val Phe Asn Phe Val Pro Cys Ser Ile Cys Ser
            100             105             110

Asn Asn Pro Thr Cys Trp Ala Ile Cys Lys Arg Ile Pro Asn Lys Lys
            115             120             125

Pro Gly Lys Lys Thr Thr Thr Lys Pro Thr Glu Glu Pro Thr Phe Lys
    130             135             140
```

-continued

```
Thr Ala Lys Glu Asp Pro Lys Pro Gln Thr Thr Gly Ser Gly Glu Val
145                 150                 155                 160

Pro Thr Thr Lys Pro Thr Gly Glu Pro Thr Ile Asn Thr Thr Lys Thr
                165                 170                 175

Asn Ile Thr Thr Thr Leu Leu Thr Ser Asn Thr Thr Arg Asn Pro Glu
                180                 185                 190

Leu Thr Ser Gln Met Glu Thr Phe His Ser Thr Ser Ser Glu Gly Asn
            195                 200                 205

Pro Ser Pro Ser Gln Val Ser Ile Thr Ser Glu Tyr Leu Ser Gln Pro
        210                 215                 220

Ser Ser Pro Pro Asn Thr Pro Arg
225                 230
```

```
<210> SEQ ID NO 5
<211> LENGTH: 158
<212> TYPE: PRT
<213> ORGANISM: Artificial
<220> FEATURE:
<223> OTHER INFORMATION: The sequence is artificially synthesized.

<400> SEQUENCE: 5

Ala Leu Glu Val Leu Phe Gln Gly Pro Tyr Glu Val Arg Asn Val Ser
1                   5                   10                  15

Gly Ile Tyr His Val Thr Asn Asp Cys Ser Asn Ser Ser Ile Val Tyr
                20                  25                  30

Glu Ala Ala Asp Val Ile Met His Thr Pro Gly Cys Val Pro Cys Val
            35                  40                  45

Arg Glu Gly Asn Ser Ser Arg Cys Trp Val Ala Leu Thr Pro Thr Leu
        50                  55                  60

Ala Ala Arg Asn Ala Ser Val Pro Thr Thr Thr Ile Arg Arg His Val
65                  70                  75                  80

Asp Leu Leu Val Gly Thr Ala Ala Phe Cys Ser Ala Met Tyr Val Gly
                85                  90                  95

Asp Leu Cys Gly Ser Ile Phe Leu Val Ser Gln Leu Phe Thr Phe Ser
                100                 105                 110

Pro Arg Arg His Glu Thr Val Gln Asp Cys Asn Cys Ser Ile Tyr Pro
            115                 120                 125

Gly His Val Ser Gly His Arg Met Ala Trp Asp Met Met Met Asn Trp
        130                 135                 140

Ser Pro Thr Thr Ala Leu Val Val Ser Gln Leu Leu Arg Ile
145                 150                 155
```

```
<210> SEQ ID NO 6
<211> LENGTH: 278
<212> TYPE: PRT
<213> ORGANISM: Artificial
<220> FEATURE:
<223> OTHER INFORMATION: The sequence is artificially synthesized.

<400> SEQUENCE: 6

Glu Thr His Thr Thr Gly Arg Val Ala Gly His Thr Thr Ser Gly Phe
1                   5                   10                  15

Thr Ser Leu Phe Ser Ser Gly Ala Ser Gln Lys Ile Gln Leu Val Asn
                20                  25                  30

Thr Asn Gly Ser Trp His Ile Asn Arg Thr Ala Leu Asn Cys Asn Asp
            35                  40                  45

Ser Leu Gln Thr Gly Phe Phe Ala Ala Leu Phe Tyr Ala His Lys Phe
        50                  55                  60
```

-continued

```
Asn Ser Ser Gly Cys Pro Glu Arg Met Ala Ser Cys Arg Pro Ile Asp
65              70              75              80

Trp Phe Ala Gln Gly Trp Gly Pro Ile Thr Tyr Thr Lys Pro Asn Ser
            85              90              95

Ser Asp Gln Arg Pro Tyr Cys Trp His Tyr Ala Pro Arg Pro Cys Gly
            100             105             110

Val Val Pro Ala Ser Gln Val Cys Gly Pro Val Tyr Cys Phe Thr Pro
            115             120             125

Ser Pro Val Val Val Gly Thr Thr Asp Arg Ser Gly Val Pro Thr Tyr
        130             135             140

Ser Trp Gly Glu Asn Glu Thr Asp Met Met Leu Leu Asn Asn Thr Arg
145             150             155             160

Pro Pro Gln Gly Asn Trp Phe Gly Cys Thr Trp Met Asn Ser Thr Gly
            165             170             175

Phe Thr Lys Thr Cys Gly Gly Pro Pro Cys Asn Ile Gly Gly Val Gly
            180             185             190

Asn Arg Thr Leu Ile Cys Pro Thr Asp Cys Phe Arg Lys His Pro Glu
            195             200             205

Ala Thr Tyr Thr Lys Cys Gly Ser Gly Pro Trp Leu Thr Pro Arg Cys
        210             215             220

Leu Val Asp Tyr Pro Tyr Arg Leu Trp His Tyr Pro Cys Thr Leu Asn
225             230             235             240

Phe Ser Ile Phe Lys Val Arg Met Tyr Val Gly Gly Val Glu His Arg
            245             250             255

Leu Asn Ala Ala Cys Asn Trp Thr Arg Gly Glu Arg Cys Asn Leu Glu
            260             265             270

Asp Arg Asp Arg Ser Glu
        275
```

```
<210> SEQ ID NO 7
<211> LENGTH: 347
<212> TYPE: PRT
<213> ORGANISM: Artificial
<220> FEATURE:
<223> OTHER INFORMATION: The sequence is artificially synthesized.

<400> SEQUENCE: 7
```

```
Asp Arg Ile Cys Thr Gly Ile Thr Ser Ser Asn Ser Pro His Val Val
1               5               10              15

Lys Thr Ala Thr Gln Gly Glu Val Asn Val Thr Gly Val Ile Pro Leu
            20              25              30

Thr Thr Thr Pro Thr Lys Ser His Phe Ala Asn Leu Lys Gly Thr Glu
            35              40              45

Thr Arg Gly Lys Leu Cys Pro Lys Cys Leu Asn Cys Thr Asp Leu Asp
        50              55              60

Val Ala Leu Gly Arg Pro Lys Cys Thr Gly Lys Ile Pro Ser Ala Arg
65              70              75              80

Val Ser Ile Leu His Glu Val Arg Pro Val Thr Ser Gly Cys Phe Pro
            85              90              95

Ile Met His Asp Arg Thr Lys Ile Arg Gln Leu Pro Asn Leu Leu Arg
            100             105             110

Gly Tyr Glu His Ile Arg Leu Ser Thr His Asn Val Ile Asn Ala Glu
            115             120             125

Asn Ala Pro Gly Gly Pro Tyr Lys Ile Gly Thr Ser Gly Ser Cys Pro
        130             135             140
```

```
Asn Ile Thr Asn Gly Asn Gly Phe Phe Ala Thr Met Ala Trp Ala Val
145             150             155             160

Pro Lys Asn Asp Lys Asn Lys Thr Ala Thr Asn Pro Leu Thr Ile Glu
            165             170             175

Val Pro Tyr Ile Cys Thr Glu Gly Glu Asp Gln Ile Thr Val Trp Gly
            180             185             190

Phe His Ser Asp Asn Glu Thr Gln Met Ala Lys Leu Tyr Gly Asp Ser
            195             200             205

Lys Pro Gln Lys Phe Thr Ser Ser Ala Asn Gly Val Thr Thr His Tyr
        210             215             220

Val Ser Gln Ile Gly Gly Phe Pro Asn Gln Thr Glu Asp Gly Gly Leu
225             230             235             240

Pro Gln Ser Gly Arg Ile Val Val Asp Tyr Met Val Gln Lys Ser Gly
            245             250             255

Lys Thr Gly Thr Ile Thr Tyr Gln Arg Gly Ile Leu Leu Pro Gln Lys
            260             265             270

Val Trp Cys Ala Ser Gly Arg Ser Lys Val Ile Lys Gly Ser Leu Pro
            275             280             285

Leu Ile Gly Glu Ala Asp Cys Leu His Glu Lys Tyr Gly Gly Leu Asn
        290             295             300

Lys Ser Lys Pro Tyr Tyr Thr Gly Glu His Ala Lys Ala Ile Gly Asn
305             310             315             320

Cys Pro Ile Trp Val Lys Thr Pro Leu Lys Leu Ala Asn Gly Thr Lys
            325             330             335

Tyr Arg Pro Pro Ala Lys Leu Leu Lys Glu Arg
            340             345
```

```
<210> SEQ ID NO 8
<211> LENGTH: 511
<212> TYPE: PRT
<213> ORGANISM: Artificial
<220> FEATURE:
<223> OTHER INFORMATION: The sequence is artificially synthesized.

<400> SEQUENCE: 8
```

```
Asp Gln Ile Cys Ile Gly Tyr His Ala Asn Asn Ser Thr Glu Gln Val
1               5               10              15

Asp Thr Ile Met Glu Lys Asn Val Thr Val Thr His Ala Gln Asp Ile
            20              25              30

Leu Glu Lys Thr His Asn Gly Lys Leu Cys Asp Leu Asp Gly Val Lys
        35              40              45

Pro Leu Ile Leu Arg Asp Cys Ser Val Ala Gly Trp Leu Leu Gly Asn
        50              55              60

Pro Met Cys Asp Glu Phe Ile Asn Val Pro Glu Trp Ser Tyr Ile Val
65              70              75              80

Glu Lys Ala Asn Pro Ala Asn Asp Leu Cys Tyr Pro Gly Asn Phe Asn
            85              90              95

Asp Tyr Glu Glu Leu Lys His Leu Leu Ser Arg Ile Asn His Phe Glu
            100             105             110

Lys Ile Gln Ile Ile Pro Lys Ser Ser Trp Ser Asp His Glu Ala Ser
        115             120             125

Ser Gly Val Ser Ser Ala Cys Pro Tyr Gln Gly Thr Pro Ser Phe Phe
        130             135             140

Arg Asn Val Val Trp Leu Ile Lys Lys Asn Asn Thr Tyr Pro Thr Ile
145             150             155             160
```

```
Lys Arg Ser Tyr Asn Asn Thr Asn Gln Glu Asp Leu Leu Ile Leu Trp
                165                 170                 175

Gly Ile His His Ser Asn Asp Ala Ala Glu Gln Thr Lys Leu Tyr Gln
                180                 185                 190

Asn Pro Thr Thr Tyr Ile Ser Val Gly Thr Ser Thr Leu Asn Gln Arg
                195                 200                 205

Leu Val Pro Lys Ile Ala Thr Arg Ser Lys Val Asn Gly Gln Ser Gly
        210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Val Lys Ser Glu Val Glu Tyr Gly
                260                 265                 270

Asn Cys Asn Thr Lys Cys Gln Thr Pro Ile Gly Ala Ile Asn Ser Ser
                275                 280                 285

Met Pro Phe His Asn Ile His Pro Leu Thr Ile Gly Glu Cys Pro Lys
        290                 295                 300

Tyr Val Lys Ser Asn Lys Leu Val Leu Ala Thr Gly Leu Arg Asn Ser
305                 310                 315                 320

Pro Leu Thr Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
                340                 345                 350

Ser Asn Glu Gln Gly Ser Gly Tyr Ala Ala Asp Lys Glu Ser Thr Gln
                355                 360                 365

Lys Ala Ile Asp Gly Val Thr Asn Lys Val Asn Ser Ile Ile Asp Lys
        370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
                420                 425                 430

Thr Leu Asp Phe His Asp Ser Asn Val Lys Asn Leu Tyr Asp Lys Val
                435                 440                 445

Arg Leu Gln Leu Arg Asp Asn Ala Lys Glu Leu Gly Asn Gly Cys Phe
        450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Thr Tyr Gln
                500                 505                 510
```

```
<210> SEQ ID NO 9
<211> LENGTH: 276
<212> TYPE: PRT
<213> ORGANISM: Artificial
<220> FEATURE:
<223> OTHER INFORMATION: The sequence is artificially synthesized.

<400> SEQUENCE: 9

Ile Pro Leu Gly Val Val His Asn Asn Thr Leu Gln Val Ser Asp Ile
1               5                   10                  15
```

-continued

```
Asp Lys Leu Val Cys Arg Asp Lys Leu Ser Ser Thr Ser Gln Leu Lys
         20                  25                  30

Ser Val Gly Leu Asn Leu Glu Gly Asn Gly Val Ala Thr Asp Val Pro
         35                  40                  45

Thr Ala Thr Lys Arg Trp Gly Phe Arg Ala Gly Val Pro Pro Lys Val
     50                  55                  60

Val Asn Tyr Glu Ala Gly Glu Trp Ala Glu Asn Cys Tyr Asn Leu Asp
65                  70                  75                  80

Ile Lys Lys Ala Asp Gly Ser Glu Cys Leu Pro Glu Ala Pro Glu Gly
                 85                  90                  95

Val Arg Gly Phe Pro Arg Cys Arg Tyr Val His Lys Val Ser Gly Thr
                100                 105                 110

Gly Pro Cys Pro Glu Gly Tyr Ala Phe His Lys Glu Gly Ala Phe Phe
             115                 120                 125

Leu Tyr Asp Arg Leu Ala Ser Thr Ile Ile Tyr Arg Ser Thr Thr Phe
         130                 135                 140

Ser Glu Gly Val Val Ala Phe Leu Ile Leu Pro Glu Thr Lys Lys Asp
145                 150                 155                 160

Phe Phe Gln Ser Pro Pro Leu His Glu Pro Ala Asn Met Thr Thr Asp
                165                 170                 175

Pro Ser Ser Tyr Tyr His Thr Val Thr Leu Asn Tyr Val Ala Asp Asn
             180                 185                 190

Phe Gly Thr Asn Met Thr Asn Phe Leu Phe Gln Val Asp His Leu Thr
             195                 200                 205

Tyr Val Gln Leu Glu Pro Arg Phe Thr Pro Gln Phe Leu Val Gln Leu
         210                 215                 220

Asn Glu Thr Ile Tyr Thr Asn Gly Arg Arg Ser Asn Thr Thr Gly Thr
225                 230                 235                 240

Leu Ile Trp Lys Val Asn Pro Thr Val Asp Thr Gly Val Gly Glu Trp
                245                 250                 255

Ala Phe Trp Glu Asn Lys Lys Asn Phe Thr Lys Thr Leu Ser Ser Glu
                260                 265                 270

Glu Leu Ser Val
         275

<210> SEQ ID NO 10
<211> LENGTH: 469
<212> TYPE: PRT
<213> ORGANISM: Artificial
<220> FEATURE:
<223> OTHER INFORMATION: The sequence is artificially synthesized.

<400> SEQUENCE: 10

Met Pro Leu Gly Val Val Thr Asn Ser Thr Leu Glu Val Thr Glu Ile
1               5                   10                  15

Asp Gln Leu Val Cys Lys Asp His Leu Ala Ser Thr Asp Gln Leu Lys
         20                  25                  30

Ser Val Gly Leu Asn Leu Glu Gly Ser Gly Val Ser Thr Asp Ile Pro
         35                  40                  45

Ser Ala Thr Lys Arg Trp Gly Phe Arg Ser Gly Val Pro Pro Lys Val
     50                  55                  60

Val Ser Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Pro Pro Asp Gly
                 85                  90                  95
```

-continued

```
Val Arg Gly Phe Pro Arg Cys Arg Tyr Val His Lys Ala Gln Gly Thr
            100             105             110

Gly Pro Cys Pro Gly Asp Tyr Ala Phe His Lys Asp Gly Ala Phe Phe
            115             120             125

Leu Tyr Asp Arg Leu Ala Ser Thr Val Ile Tyr Arg Gly Val Asn Phe
            130             135             140

Ala Glu Gly Val Ile Ala Phe Leu Ile Leu Ala Lys Pro Lys Glu Thr
145             150             155             160

Phe Leu Gln Ser Pro Pro Ile Arg Glu Ala Val Asn Tyr Thr Glu Asn
                165             170             175

Thr Ser Ser Tyr Tyr Ala Thr Ser Tyr Leu Glu Tyr Glu Ile Glu Asn
            180             185             190

Phe Gly Ala Gln His Ser Thr Thr Leu Phe Lys Ile Asp Asn Asn Thr
            195             200             205

Phe Val Arg Leu Asp Arg Pro His Thr Pro Gln Phe Leu Phe Gln Leu
            210             215             220

Asn Asp Thr Ile His Leu His Gln Gln Leu Ser Asn Thr Thr Gly Arg
225             230             235             240

Leu Ile Trp Thr Leu Asp Ala Asn Ile Asn Ala Asp Ile Gly Glu Trp
            245             250             255

Ala Phe Trp Glu Asn Lys Lys Asn Leu Ser Glu Gln Leu Arg Gly Glu
            260             265             270

Glu Leu Ser Phe Glu Ala Leu Ser Leu Asn Glu Thr Glu Asp Asp Asp
            275             280             285

Ala Ala Ser Ser Arg Ile Thr Lys Gly Arg Ile Ser Asp Arg Ala Thr
            290             295             300

Arg Lys Tyr Ser Asp Leu Val Pro Lys Asn Ser Pro Gly Met Val Pro
305             310             315             320

Leu His Ile Pro Glu Gly Glu Thr Thr Leu Pro Ser Gln Asn Ser Thr
            325             330             335

Glu Gly Arg Arg Val Gly Val Asn Thr Gln Glu Thr Ile Thr Glu Thr
            340             345             350

Ala Ala Thr Ile Ile Gly Thr Asn Gly Asn His Met Gln Ile Ser Thr
            355             360             365

Ile Gly Ile Arg Pro Ser Ser Ser Gln Ile Pro Ser Ser Ser Pro Thr
            370             375             380

Thr Ala Pro Ser Pro Glu Ala Gln Thr Pro Thr Thr His Thr Ser Gly
385             390             395             400

Pro Ser Val Met Ala Thr Glu Glu Pro Thr Thr Pro Pro Gly Ser Ser
            405             410             415

Pro Gly Pro Thr Thr Glu Ala Pro Thr Leu Thr Thr Pro Glu Asn Ile
            420             425             430

Thr Thr Ala Val Lys Thr Val Leu Pro Gln Glu Ser Thr Ser Asn Gly
            435             440             445

Leu Ile Thr Ser Thr Val Thr Gly Ile Leu Gly Ser Leu Gly Leu Arg
            450             455             460

Lys Arg Ser Arg Arg
465
```

<210> SEQ ID NO 11
<211> LENGTH: 107
<212> TYPE: PRT
<213> ORGANISM: Artificial
<220> FEATURE:

-continued

<223> OTHER INFORMATION: The sequence is artificially synthesized.

<400> SEQUENCE: 11

Val Ser Tyr Ser Leu Cys Thr Ala Ala Phe Thr Phe Thr Lys Ile Pro
1               5                   10                  15

Ala Glu Thr Leu His Gly Thr Val Thr Val Glu Val Gln Tyr Ala Gly
            20                  25                  30

Thr Asp Gly Pro Cys Lys Val Pro Ala Gln Met Ala Val Asp Met Gln
        35                  40                  45

Thr Leu Thr Pro Val Gly Arg Leu Ile Thr Ala Asn Pro Val Ile Thr
    50                  55                  60

Glu Ser Thr Glu Asn Ser Lys Met Met Leu Glu Leu Asp Pro Pro Phe
65                  70                  75                  80

Gly Asp Ser Tyr Ile Val Ile Gly Val Gly Glu Lys Lys Ile Thr His
                85                  90                  95

His Trp His Arg Ser Gly Ser Thr Ile Gly Lys
            100                 105

<210> SEQ ID NO 12
<211> LENGTH: 243
<212> TYPE: PRT
<213> ORGANISM: Artificial
<220> FEATURE:
<223> OTHER INFORMATION: The sequence is artificially synthesized.

<400> SEQUENCE: 12

Asn His Lys Val Thr Ser Thr Thr Thr Ile Ile Gln Asp Ala Thr Ser
1               5                   10                  15

Gln Ile Lys Asn Thr Thr Pro Thr Tyr Leu Thr Gln Ser Pro Gln Leu
            20                  25                  30

Gly Ile Ser Pro Ser Asn Pro Ser Glu Ile Thr Ser Gln Ile Thr Thr
        35                  40                  45

Ile Leu Ala Ser Thr Thr Pro Gly Val Lys Ser Thr Leu Gln Ser Thr
    50                  55                  60

Thr Val Gly Thr Lys Asn Thr Thr Thr Gln Ala Gln Pro Ser Lys
65                  70                  75                  80

Pro Thr Thr Lys Gln Arg Gln Asn Lys Pro Pro Ser Lys Pro Asn Asn
            85                  90                  95

Asp Phe His Phe Glu Val Phe Asn Phe Val Pro Cys Ser Ile Cys Ser
            100                 105                 110

Asn Asn Pro Thr Cys Trp Ala Ile Cys Lys Arg Ile Pro Asn Lys Lys
            115                 120                 125

Pro Gly Lys Lys Thr Thr Thr Lys Pro Thr Glu Glu Pro Thr Phe Lys
        130                 135                 140

Thr Ala Lys Glu Asp Pro Lys Pro Gln Thr Thr Gly Ser Gly Glu Val
145                 150                 155                 160

Pro Thr Thr Lys Pro Thr Gly Glu Pro Thr Ile Asn Thr Thr Lys Thr
                165                 170                 175

Asn Ile Thr Thr Thr Leu Leu Thr Ser Asn Thr Thr Arg Asn Pro Glu
            180                 185                 190

Leu Thr Ser Gln Met Glu Thr Phe His Ser Thr Ser Ser Glu Gly Asn
        195                 200                 205

Pro Ser Pro Ser Gln Val Ser Ile Thr Ser Glu Tyr Leu Ser Gln Pro
    210                 215                 220

Ser Ser Pro Pro Asn Thr Pro Arg Ala His His His His His His His
225                 230                 235                 240

His His His

<210> SEQ ID NO 13
<211> LENGTH: 168
<212> TYPE: PRT
<213> ORGANISM: Artificial
<220> FEATURE:
<223> OTHER INFORMATION: The sequence is artificially synthesized.

<400> SEQUENCE: 13

```
His His His His His His His His His His Ala Leu Glu Val Leu Phe
1               5                   10                  15

Gln Gly Pro Tyr Glu Val Arg Asn Val Ser Gly Ile Tyr His Val Thr
            20                  25                  30

Asn Asp Cys Ser Asn Ser Ser Ile Val Tyr Glu Ala Ala Asp Val Ile
            35                  40                  45

Met His Thr Pro Gly Cys Val Pro Cys Val Arg Glu Gly Asn Ser Ser
        50                  55                  60

Arg Cys Trp Val Ala Leu Thr Pro Thr Leu Ala Ala Arg Asn Ala Ser
65                  70                  75                  80

Val Pro Thr Thr Thr Ile Arg Arg His Val Asp Leu Leu Val Gly Thr
                85                  90                  95

Ala Ala Phe Cys Ser Ala Met Tyr Val Gly Asp Leu Cys Gly Ser Ile
            100                 105                 110

Phe Leu Val Ser Gln Leu Phe Thr Phe Ser Pro Arg Arg His Glu Thr
            115                 120                 125

Val Gln Asp Cys Asn Cys Ser Ile Tyr Pro Gly His Val Ser Gly His
        130                 135                 140

Arg Met Ala Trp Asp Met Met Met Asn Trp Ser Pro Thr Thr Ala Leu
145                 150                 155                 160

Val Val Ser Gln Leu Leu Arg Ile
                165
```

<210> SEQ ID NO 14
<211> LENGTH: 289
<212> TYPE: PRT
<213> ORGANISM: Artificial
<220> FEATURE:
<223> OTHER INFORMATION: The sequence is artificially synthesized.

<400> SEQUENCE: 14

```
Glu Thr His Thr Thr Gly Arg Val Ala Gly His Thr Thr Ser Gly Phe
1               5                   10                  15

Thr Ser Leu Phe Ser Ser Gly Ala Ser Gln Lys Ile Gln Leu Val Asn
            20                  25                  30

Thr Asn Gly Ser Trp His Ile Asn Arg Thr Ala Leu Asn Cys Asn Asp
            35                  40                  45

Ser Leu Gln Thr Gly Phe Phe Ala Ala Leu Phe Tyr Ala His Lys Phe
        50                  55                  60

Asn Ser Ser Gly Cys Pro Glu Arg Met Ala Ser Cys Arg Pro Ile Asp
65                  70                  75                  80

Trp Phe Ala Gln Gly Trp Gly Pro Ile Thr Tyr Thr Lys Pro Asn Ser
                85                  90                  95

Ser Asp Gln Arg Pro Tyr Cys Trp His Tyr Ala Pro Arg Pro Cys Gly
            100                 105                 110

Val Val Pro Ala Ser Gln Val Cys Gly Pro Val Tyr Cys Phe Thr Pro
            115                 120                 125
```

-continued

```
Ser Pro Val Val Val Gly Thr Thr Asp Arg Ser Gly Val Pro Thr Tyr
    130             135             140
```

```
Ser Trp Gly Glu Asn Glu Thr Asp Met Met Leu Leu Asn Asn Thr Arg
145             150             155             160
```

```
Pro Pro Gln Gly Asn Trp Phe Gly Cys Thr Trp Met Asn Ser Thr Gly
            165             170             175
```

```
Phe Thr Lys Thr Cys Gly Gly Pro Pro Cys Asn Ile Gly Gly Val Gly
            180             185             190
```

```
Asn Arg Thr Leu Ile Cys Pro Thr Asp Cys Phe Arg Lys His Pro Glu
            195             200             205
```

```
Ala Thr Tyr Thr Lys Cys Gly Ser Gly Pro Trp Leu Thr Pro Arg Cys
            210             215             220
```

```
Leu Val Asp Tyr Pro Tyr Arg Leu Trp His Tyr Pro Cys Thr Leu Asn
225             230             235             240
```

```
Phe Ser Ile Phe Lys Val Arg Met Tyr Val Gly Gly Val Glu His Arg
            245             250             255
```

```
Leu Asn Ala Ala Cys Asn Trp Thr Arg Gly Glu Arg Cys Asn Leu Glu
            260             265             270
```

```
Asp Arg Asp Arg Ser Glu Ala His His His His His His His His
            275             280             285
```

```
His
```

```
<210> SEQ ID NO 15
<211> LENGTH: 358
<212> TYPE: PRT
<213> ORGANISM: Artificial
<220> FEATURE:
<223> OTHER INFORMATION: The sequence is artificially synthesized.
```

```
<400> SEQUENCE: 15
```

```
Asp Arg Ile Cys Thr Gly Ile Thr Ser Ser Asn Ser Pro His Val Val
1               5               10              15
```

```
Lys Thr Ala Thr Gln Gly Glu Val Asn Val Thr Gly Val Ile Pro Leu
            20              25              30
```

```
Thr Thr Thr Pro Thr Lys Ser His Phe Ala Asn Leu Lys Gly Thr Glu
        35              40              45
```

```
Thr Arg Gly Lys Leu Cys Pro Lys Cys Leu Asn Cys Thr Asp Leu Asp
    50              55              60
```

```
Val Ala Leu Gly Arg Pro Lys Cys Thr Gly Lys Ile Pro Ser Ala Arg
65              70              75              80
```

```
Val Ser Ile Leu His Glu Val Arg Pro Val Thr Ser Gly Cys Phe Pro
            85              90              95
```

```
Ile Met His Asp Arg Thr Lys Ile Arg Gln Leu Pro Asn Leu Leu Arg
            100             105             110
```

```
Gly Tyr Glu His Ile Arg Leu Ser Thr His Asn Val Ile Asn Ala Glu
            115             120             125
```

```
Asn Ala Pro Gly Gly Pro Tyr Lys Ile Gly Thr Ser Gly Ser Cys Pro
            130             135             140
```

```
Asn Ile Thr Asn Gly Asn Gly Phe Phe Ala Thr Met Ala Trp Ala Val
145             150             155             160
```

```
Pro Lys Asn Asp Lys Asn Lys Thr Ala Thr Asn Pro Leu Thr Ile Glu
            165             170             175
```

```
Val Pro Tyr Ile Cys Thr Glu Gly Glu Asp Gln Ile Thr Val Trp Gly
            180             185             190
```

```
Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
                260                 265                 270

Val Trp Cys Ala Ser Gly Arg Ser Lys Val Ile Lys Gly Ser Leu Pro
                275                 280                 285

Leu Ile Gly Glu Ala Asp Cys Leu His Glu Lys Tyr Gly Gly Leu Asn
        290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Ala His His His His
                340                 345                 350

His His His His His His
        355
```

```
<210> SEQ ID NO 16
<211> LENGTH: 522
<212> TYPE: PRT
<213> ORGANISM: Artificial
<220> FEATURE:
<223> OTHER INFORMATION: The sequence is artificially synthesized.

<400> SEQUENCE: 16

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Thr Pro Ser Phe Phe
        130                 135                 140

Arg Asn Val Val Trp Leu Ile Lys Lys Asn Asn Thr Tyr Pro Thr Ile
145                 150                 155                 160

Lys Arg Ser Tyr Asn Asn Thr Asn Gln Glu Asp Leu Leu Ile Leu Trp
                165                 170                 175

Gly Ile His His Ser Asn Asp Ala Ala Glu Gln Thr Lys Leu Tyr Gln
                180                 185                 190
```

```
Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
        210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Val Lys Ser Glu Val Glu Tyr Gly
                260                 265                 270

Asn Cys Asn Thr Lys Cys Gln Thr Pro Ile Gly Ala Ile Asn Ser Ser
                275                 280                 285

Met Pro Phe His Asn Ile His Pro Leu Thr Ile Gly Glu Cys Pro Lys
        290                 295                 300

Tyr Val Lys Ser Asn Lys Leu Val Leu Ala Thr Gly Leu Arg Asn Ser
305                 310                 315                 320

Pro Leu Thr Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
                340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
        370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
                420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
        450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Thr Tyr Gln Ala
                500                 505                 510

His His His His His His His His His His
        515                 520
```

<210> SEQ ID NO 17
<211> LENGTH: 514
<212> TYPE: PRT
<213> ORGANISM: Artificial
<220> FEATURE:
<223> OTHER INFORMATION: The sequence is artificially synthesized.

<400> SEQUENCE: 17

```
Ile Pro Leu Gly Val Val His Asn Asn Thr Leu Gln Val Ser Asp Ile
1               5                   10                  15

Asp Lys Leu Val Cys Arg Asp Lys Leu Ser Ser Thr Ser Gln Leu Lys
        20                  25                  30
```

-continued

```
Ser Val Gly Leu Asn Leu Glu Gly Asn Gly Val Ala Thr Asp Val Pro
        35              40              45

Thr Ala Thr Lys Arg Trp Gly Phe Arg Ala Gly Val Pro Pro Lys Val
    50              55              60

Val Asn Tyr Glu Ala Gly Glu Trp Ala Glu Asn Cys Tyr Asn Leu Asp
65              70              75              80

Ile Lys Lys Ala Asp Gly Ser Glu Cys Leu Pro Glu Ala Pro Glu Gly
            85              90              95

Val Arg Gly Phe Pro Arg Cys Arg Tyr Val His Lys Val Ser Gly Thr
            100             105             110

Gly Pro Cys Pro Glu Gly Tyr Ala Phe His Lys Glu Gly Ala Phe Phe
        115             120             125

Leu Tyr Asp Arg Leu Ala Ser Thr Ile Ile Tyr Arg Ser Thr Thr Phe
    130             135             140

Ser Glu Gly Val Val Ala Phe Leu Ile Leu Pro Glu Thr Lys Lys Asp
145             150             155             160

Phe Phe Gln Ser Pro Pro Leu His Glu Pro Ala Asn Met Thr Thr Asp
            165             170             175

Pro Ser Ser Tyr Tyr His Thr Val Thr Leu Asn Tyr Val Ala Asp Asn
            180             185             190

Phe Gly Thr Asn Met Thr Asn Phe Leu Phe Gln Val Asp His Leu Thr
            195             200             205

Tyr Val Gln Leu Glu Pro Arg Phe Thr Pro Gln Phe Leu Val Gln Leu
    210             215             220

Asn Glu Thr Ile Tyr Thr Asn Gly Arg Arg Ser Asn Thr Thr Gly Thr
225             230             235             240

Leu Ile Trp Lys Val Asn Pro Thr Val Asp Thr Gly Val Gly Glu Trp
            245             250             255

Ala Phe Trp Glu Asn Lys Lys Asn Phe Thr Lys Thr Leu Ser Ser Glu
            260             265             270

Glu Leu Ser Val Ala Asp Asp Asp Lys Glu Pro Lys Ser Ser Asp
    275             280             285

Lys Thr His Thr Cys Pro Pro Cys Pro Ala Pro Glu Leu Leu Gly Gly
    290             295             300

Pro Ser Val Phe Leu Phe Pro Pro Lys Pro Lys Asp Thr Leu Met Ile
305             310             315             320

Ser Arg Thr Pro Glu Val Thr Cys Val Val Val Asp Val Ser His Glu
            325             330             335

Asp Pro Glu Val Lys Phe Asn Trp Tyr Val Asp Gly Val Glu Val His
            340             345             350

Asn Ala Lys Thr Lys Pro Arg Glu Glu Gln Tyr Asn Ser Thr Tyr Arg
            355             360             365

Val Val Ser Val Leu Thr Val Leu His Gln Asp Trp Leu Asn Gly Lys
    370             375             380

Glu Tyr Lys Cys Lys Val Ser Asn Lys Ala Leu Pro Ala Pro Ile Glu
385             390             395             400

Lys Thr Ile Ser Lys Ala Lys Gly Gln Pro Arg Glu Pro Gln Val Tyr
            405             410             415

Thr Leu Pro Pro Ser Arg Asp Glu Leu Thr Lys Asn Gln Val Ser Leu
            420             425             430

Thr Cys Leu Val Lys Gly Phe Tyr Pro Ser Asp Ile Ala Val Glu Trp
            435             440             445

Glu Ser Asn Gly Gln Pro Glu Asn Asn Tyr Lys Thr Thr Pro Pro Val
```

-continued

```
           450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
                500                 505                 510

Gly Lys

<210> SEQ ID NO 18
<211> LENGTH: 480
<212> TYPE: PRT
<213> ORGANISM: Artificial
<220> FEATURE:
<223> OTHER INFORMATION: The sequence is artificially synthesized.

<400> SEQUENCE: 18

Met Pro Leu Gly Val Val Thr Asn Ser Thr Leu Glu Val Thr Glu Ile
1               5                   10                  15

Asp Gln Leu Val Cys Lys Asp His Leu Ala Ser Thr Asp Gln Leu Lys
                20                  25                  30

Ser Val Gly Leu Asn Leu Glu Gly Ser Gly Val Ser Thr Asp Ile Pro
            35                  40                  45

Ser Ala Thr Lys Arg Trp Gly Phe Arg Ser Gly Val Pro Pro Lys Val
        50                  55                  60

Val Ser Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Pro Pro Asp Gly
                85                  90                  95

Val Arg Gly Phe Pro Arg Cys Arg Tyr Val His Lys Ala Gln Gly Thr
            100                 105                 110

Gly Pro Cys Pro Gly Asp Tyr Ala Phe His Lys Asp Gly Ala Phe Phe
            115                 120                 125

Leu Tyr Asp Arg Leu Ala Ser Thr Val Ile Tyr Arg Gly Val Asn Phe
        130                 135                 140

Ala Glu Gly Val Ile Ala Phe Leu Ile Leu Ala Lys Pro Lys Glu Thr
145                 150                 155                 160

Phe Leu Gln Ser Pro Pro Ile Arg Glu Ala Val Asn Tyr Thr Glu Asn
                165                 170                 175

Thr Ser Ser Tyr Tyr Ala Thr Ser Tyr Leu Glu Tyr Glu Ile Glu Asn
            180                 185                 190

Phe Gly Ala Gln His Ser Thr Thr Leu Phe Lys Ile Asp Asn Asn Thr
            195                 200                 205

Phe Val Arg Leu Asp Arg Pro His Thr Pro Gln Phe Leu Phe Gln Leu
        210                 215                 220

Asn Asp Thr Ile His Leu His Gln Gln Leu Ser Asn Thr Thr Gly Arg
225                 230                 235                 240

Leu Ile Trp Thr Leu Asp Ala Asn Ile Asn Ala Asp Ile Gly Glu Trp
                245                 250                 255

Ala Phe Trp Glu Asn Lys Lys Asn Leu Ser Glu Gln Leu Arg Gly Glu
            260                 265                 270

Glu Leu Ser Phe Glu Ala Leu Ser Leu Asn Glu Thr Glu Asp Asp Asp
        275                 280                 285

Ala Ala Ser Ser Arg Ile Thr Lys Gly Arg Ile Ser Asp Arg Ala Thr
        290                 295                 300
```

-continued

```
Arg Lys Tyr Ser Asp Leu Val Pro Lys Asn Ser Pro Gly Met Val Pro
305                 310                 315                 320

Leu His Ile Pro Glu Gly Glu Thr Thr Leu Pro Ser Gln Asn Ser Thr
                325                 330                 335

Glu Gly Arg Arg Val Gly Val Asn Thr Gln Glu Thr Ile Thr Glu Thr
            340                 345                 350

Ala Ala Thr Ile Ile Gly Thr Asn Gly Asn His Met Gln Ile Ser Thr
            355                 360                 365

Ile Gly Ile Arg Pro Ser Ser Ser Gln Ile Pro Ser Ser Ser Pro Thr
        370                 375                 380

Thr Ala Pro Ser Pro Glu Ala Gln Thr Pro Thr Thr His Thr Ser Gly
385                 390                 395                 400

Pro Ser Val Met Ala Thr Glu Glu Pro Thr Thr Pro Pro Gly Ser Ser
                405                 410                 415

Pro Gly Pro Thr Thr Glu Ala Pro Thr Leu Thr Thr Pro Glu Asn Ile
            420                 425                 430

Thr Thr Ala Val Lys Thr Val Leu Pro Gln Glu Ser Thr Ser Asn Gly
            435                 440                 445

Leu Ile Thr Ser Thr Val Thr Gly Ile Leu Gly Ser Leu Gly Leu Arg
        450                 455                 460

Lys Arg Ser Arg Arg Ala His His His His His His His His His His
465                 470                 475                 480
```

```
<210> SEQ ID NO 19
<211> LENGTH: 345
<212> TYPE: PRT
<213> ORGANISM: Artificial
<220> FEATURE:
<223> OTHER INFORMATION: The sequence is artificially synthesized.

<400> SEQUENCE: 19
```

```
Val Ser Tyr Ser Leu Cys Thr Ala Ala Phe Thr Phe Thr Lys Ile Pro
1               5                   10                  15

Ala Glu Thr Leu His Gly Thr Val Thr Val Glu Val Gln Tyr Ala Gly
                20                  25                  30

Thr Asp Gly Pro Cys Lys Val Pro Ala Gln Met Ala Val Asp Met Gln
            35                  40                  45

Thr Leu Thr Pro Val Gly Arg Leu Ile Thr Ala Asn Pro Val Ile Thr
        50                  55                  60

Glu Ser Thr Glu Asn Ser Lys Met Met Leu Glu Leu Asp Pro Pro Phe
65                  70                  75                  80

Gly Asp Ser Tyr Ile Val Ile Gly Val Gly Glu Lys Lys Ile Thr His
                85                  90                  95

His Trp His Arg Ser Gly Ser Thr Ile Gly Lys Ala Asp Asp Asp Asp
            100                 105                 110

Lys Glu Pro Lys Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
        130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
                180                 185                 190
```

-continued

```
Gln Tyr Asn Ser Thr Tyr Arg Val Val Ser Val Leu Thr Val Leu His
        195             200             205

Gln Asp Trp Leu Asn Gly Lys Glu Tyr Lys Cys Lys Val Ser Asn Lys
    210             215             220

Ala Leu Pro Ala Pro Ile Glu Lys Thr Ile Ser Lys Ala Lys Gly Gln
225             230             235             240

Pro Arg Glu Pro Gln Val Tyr Thr Leu Pro Pro Ser Arg Asp Glu Leu
            245             250             255

Thr Lys Asn Gln Val Ser Leu Thr Cys Leu Val Lys Gly Phe Tyr Pro
            260             265             270

Ser Asp Ile Ala Val Glu Trp Glu Ser Asn Gly Gln Pro Glu Asn Asn
        275             280             285

Tyr Lys Thr Thr Pro Pro Val Leu Asp Ser Asp Gly Ser Phe Phe Leu
    290             295             300

Tyr Ser Lys Leu Thr Val Asp Lys Ser Arg Trp Gln Gln Gly Asn Val
305             310             315             320

Phe Ser Cys Ser Val Met His Glu Ala Leu His Asn His Tyr Thr Gln
            325             330             335

Lys Ser Leu Ser Leu Ser Pro Gly Lys
        340             345
```